US012582405B2

(12) United States Patent
Okada

(10) Patent No.: US 12,582,405 B2
(45) Date of Patent: Mar. 24, 2026

(54) CARTRIDGE AND CARTRIDGE SYSTEM

(71) Applicant: OLYMPUS MEDICAL SYSTEMS CORP., Tokyo (JP)

(72) Inventor: Tsutomu Okada, Tachikawa (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 122 days.

(21) Appl. No.: 18/427,101

(22) Filed: Jan. 30, 2024

(65) Prior Publication Data
US 2024/0260968 A1      Aug. 8, 2024

Related U.S. Application Data

(60) Provisional application No. 63/483,082, filed on Feb. 3, 2023.

(51) Int. Cl.
*A61B 17/122*        (2006.01)
*A61B 17/00*         (2006.01)

(52) U.S. Cl.
CPC .... *A61B 17/1222* (2013.01); *A61B 17/00234* (2013.01); *A61B 2017/00982* (2013.01)

(58) Field of Classification Search
CPC .......... A61B 17/1222; A61B 17/00234; A61B 2017/00982; A61B 17/1227; A61B 2017/00902; A61B 17/1285; A61B 2017/0053; A61B 17/122; A61B 17/128; A61B 17/12; A61B 17/105; A61B 17/072; A61B 17/068; A61B 2017/00398; A61B 17/07207; A61B 2017/07214; A61B 2017/07271; A61B 17/083; A61B 17/10
See application file for complete search history.

(56) References Cited

U.S. PATENT DOCUMENTS

2007/0112359 A1      5/2007   Kimura et al.
2022/0401106 A1     12/2022   Okada
2024/0260969 A1      8/2024   Okada

FOREIGN PATENT DOCUMENTS

WO      WO-2021171407 A1 *   9/2021   ......... A61B 17/1285

OTHER PUBLICATIONS

U.S. Appl. No. 18/427,178, Non Final Office Action mailed Jul. 31, 2025, 15 pgs.

* cited by examiner

*Primary Examiner* — Tan-Uyen T Ho
*Assistant Examiner* — Bridget E. Rabaglia
(74) *Attorney, Agent, or Firm* — Schwegman Lundberg & Woessner, P.A.

(57)      ABSTRACT
A cartridge configured to store a clip unit is described herein. The cartridge body having a storage area configured to store at least a part of the clip unit. The sheath connection portion is configured to receive a sheath of an applicator. The storage area includes a first area and a second area. The first area is configured to retract wings of the clip unit and configured to prevent a connection arm from connecting to the applicator. The second area is configured to connect the connection arm with the applicator.

19 Claims, 38 Drawing Sheets

FIG. 7

CARTRIDGE AND CARTRIDGE SYSTEM

CROSS-REFERENCE TO RELATED APPLICATIONS

The present application claims priority based on U.S. patent Provisional Application No. 63/483,082 provisionally filed in the United States on Feb. 3, 2023, the contents of which are incorporated herein by reference.

TECHNICAL FIELD

The present disclosure relates to a cartridge and a cartridge system.

BACKGROUND

In endoscopic therapy, a clip unit that can be used to ligate an excised part or the like after treatment to stop bleeding and the like. The clip unit can include a clip that nips an excised part or the like and a presser tube that accommodates the clip and can lock the clip in a closed state. The clip unit can be introduced into a treatment position by an applicator (an introduction device) which can be inserted into a channel of an endoscope.

United States patent Application, Publication No. 2007/0112359 (Patent Document 1) discusses a cartridge system that can reload a clip unit into an applicator. A user can reload a clip unit using the cartridge system.

SUMMARY

In the cartridge system disclosed in Patent Document 1, after a clip unit has been loaded into the applicator from a cartridge, a new clip unit cannot be reloaded into the empty cartridge. The cartridge is discarded whenever a clip unit is reloaded.

In consideration of the aforementioned circumstances, the present disclosure provides a cartridge and a cartridge system that can re-store a clip unit and repeatedly reload a clip unit into an applicator.

A cartridge according to a first aspect of the present disclosure is A cartridge configured to store a clip unit is described herein. The cartridge body having a storage area configured to store at least a part of the clip unit. The sheath connection portion is configured to receive a sheath of an applicator. The storage area includes a first area and a second area. The first area is configured to retract wings of the clip unit and configured to prevent a connection arm from connecting to the applicator. The second area is configured to connect the connection arm with the applicator.

With the cartridge and the cartridge system according to the present disclosure, it is possible to re-store a clip unit and to repeatedly reload a clip unit into an applicator.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 is a sectional view of the cartridge.

DETAILED DESCRIPTION

First Embodiment

A first embodiment of the present disclosure will be described below with reference to FIGS. 1 to 30.

Figure 8:
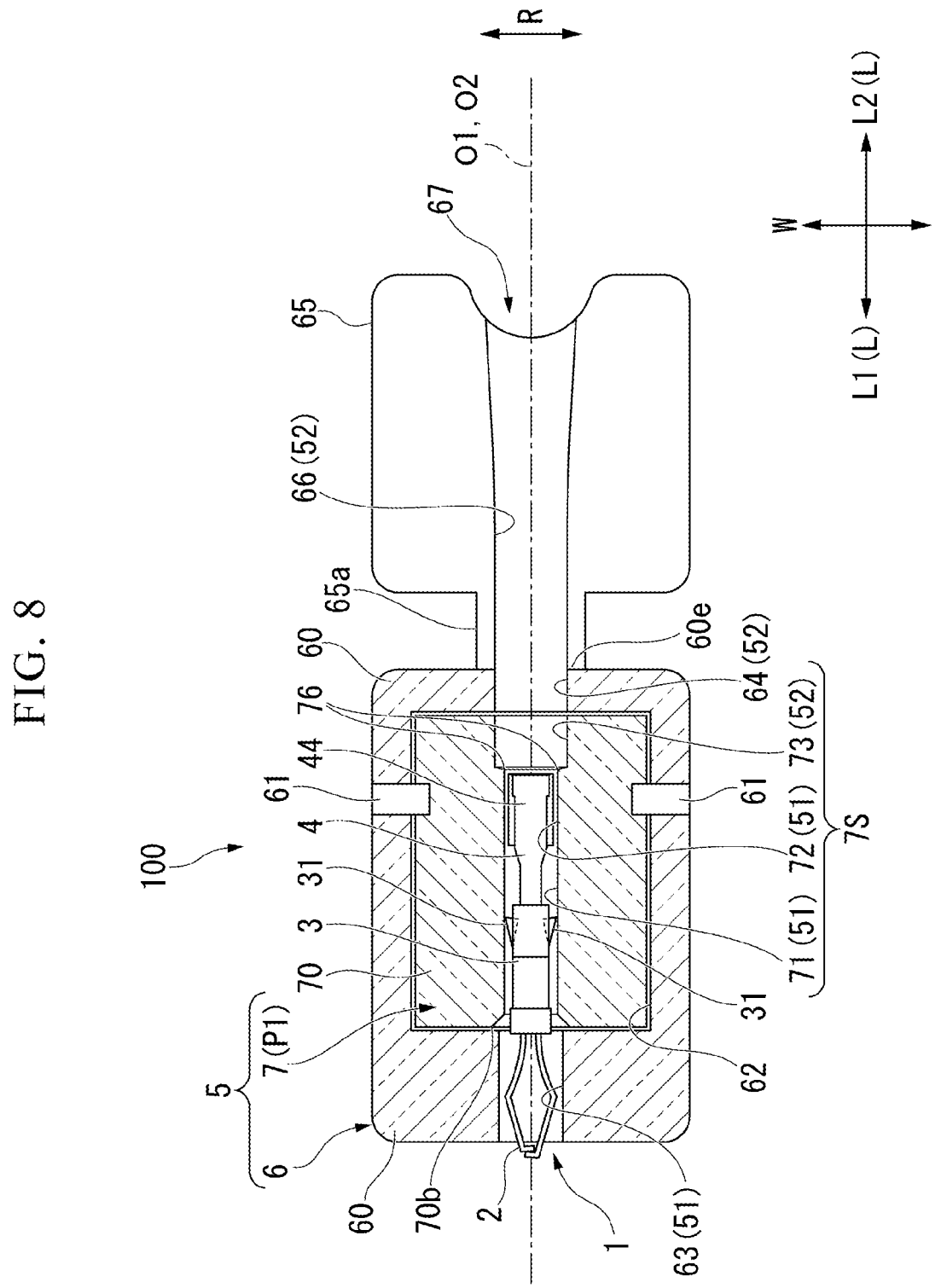
FIG. 8 is a sectional view of the cartridge in which the clip unit is stored.

A cartridge system 100 according to this embodiment may include a clip unit 1 and a cartridge 5 configured to accommodate or store the clip unit 1 (see FIG. 8). The cartridge system 100 may be a support system that allows the clip unit 1 to be easily loaded into a clip introduction device 200. The clip introduction device 200 and the clip unit 1 loaded into the clip introduction device 200 are also referred to as a clip device 300 (see FIG. 26).

Clip Introduction Device 200

Figure 1:
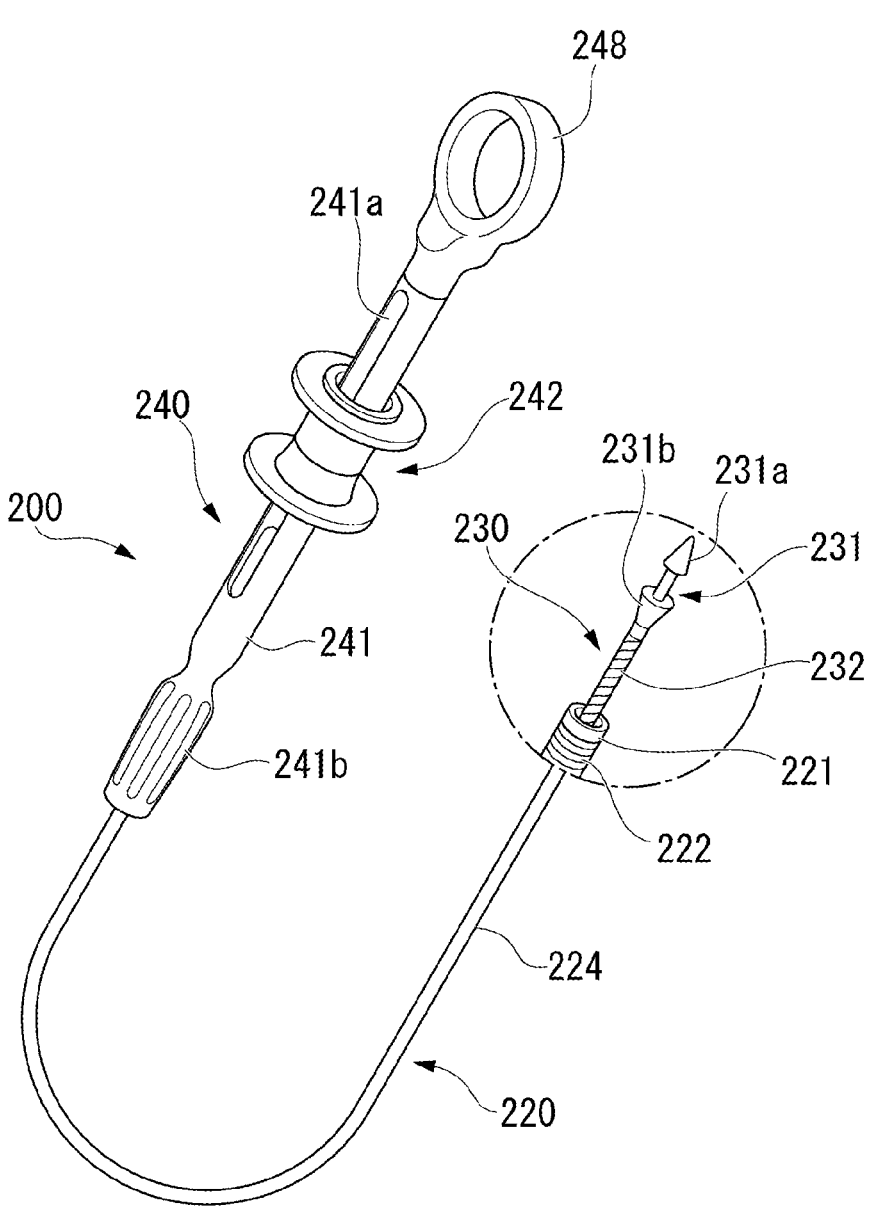
FIG. 1 is a perspective view of a clip introduction device.

FIG. 1 is a perspective view of the clip introduction device 200.

The clip introduction device (applicator) 200 may include a sheath 220, an operating wire 230, and an operation portion 240. The clip introduction device 200 may be inserted into, for example, a treatment tool insertion channel of an endoscope and may be used in combination with the endoscope. Accordingly, the sheath 220 may be formed to be much longer than a length of the treatment tool insertion channel of the endoscope. The sheath 220 may have flexibility (e.g., a portion of the sheath may be flexible) and may be curved according to curvature of an insertion portion of the endoscope.

The sheath 220 may include a distal tip 221, a distal-side coil 222, and a proximal-side coil 224 and may be formed in a long and thin tubular shape as a whole. The distal-side coil 222 may be disposed on the tip side of the sheath 220. The distal tip 221 may be disposed at the tip of the distal-side coil 222.

As illustrated in FIG. 1, the operating wire (power transmission portion) 230 may include an arrowhead-shaped hook portion (connection portion) 231 connected to the clip unit 1 and a wire 232 used to operate the arrowhead-shaped hook portion 231.

The arrowhead-shaped hook portion 231 may include an engagement portion 231*a* with a substantially conic shape engaging with the clip unit 1 and a wire connection portion 231*b* provided at a base end of the engagement portion 231*a*. The arrowhead-shaped hook portion 231 may be formed of, for example, a metallic material such as a stainless steel material.

The wire 232 may be movably inserted into the sheath 220. A tip of the wire 232 may be fixed to a base end of the wire connection portion 231*b*, for example, by welding.

As illustrated in FIG. 1, the operation portion 240 may include an operation portion body 241, a slider 242, and a thumb ring 248. The operation portion body 241, the slider 242, and the thumb ring 248 may be formed, for example, by injection-molding a resin material. The operation portion body 241 may include a slit portion 241*a* and a rotary grip 241*b* on a tip side thereof. The slit portion 241*a* supports the slider 242 such that the slider 242 is movable.

The slider 242 may be attached to be movable in a longitudinal axis direction of the operation portion body 241, and a base end of the wire 232 is attached thereto. When the slider 242 moves forward and backward along the operation portion body 241, the wire 232 moves forward and backward relative to the sheath 220, and thus the arrowhead-shaped hook portion 231 moves forward and backward.

The thumb ring 248 may be attached to the base end of the operation portion body 241 such that the thumb ring 248 can rotate around the longitudinal axis of the operation portion body 241.

Clip Unit 1

Figure 2:
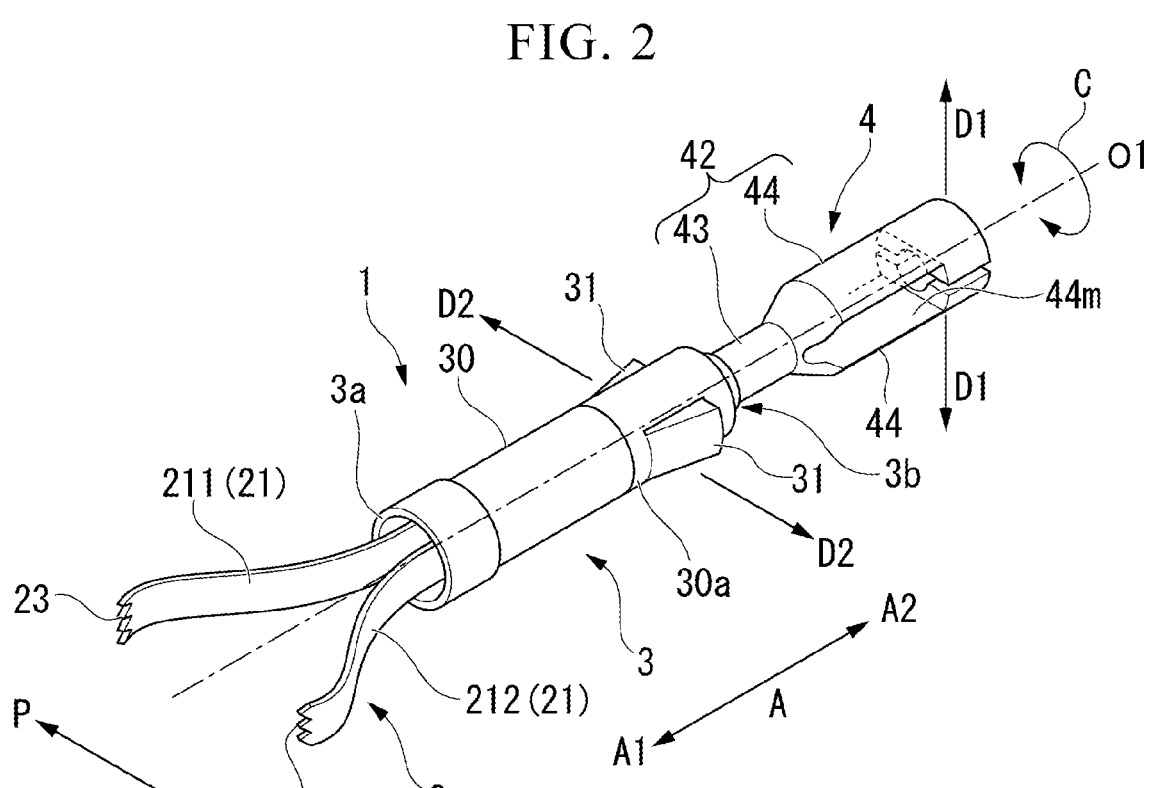
FIG. 2 is a perspective view of a clip unit of a cartridge system according to the first embodiment.
Figure 3:
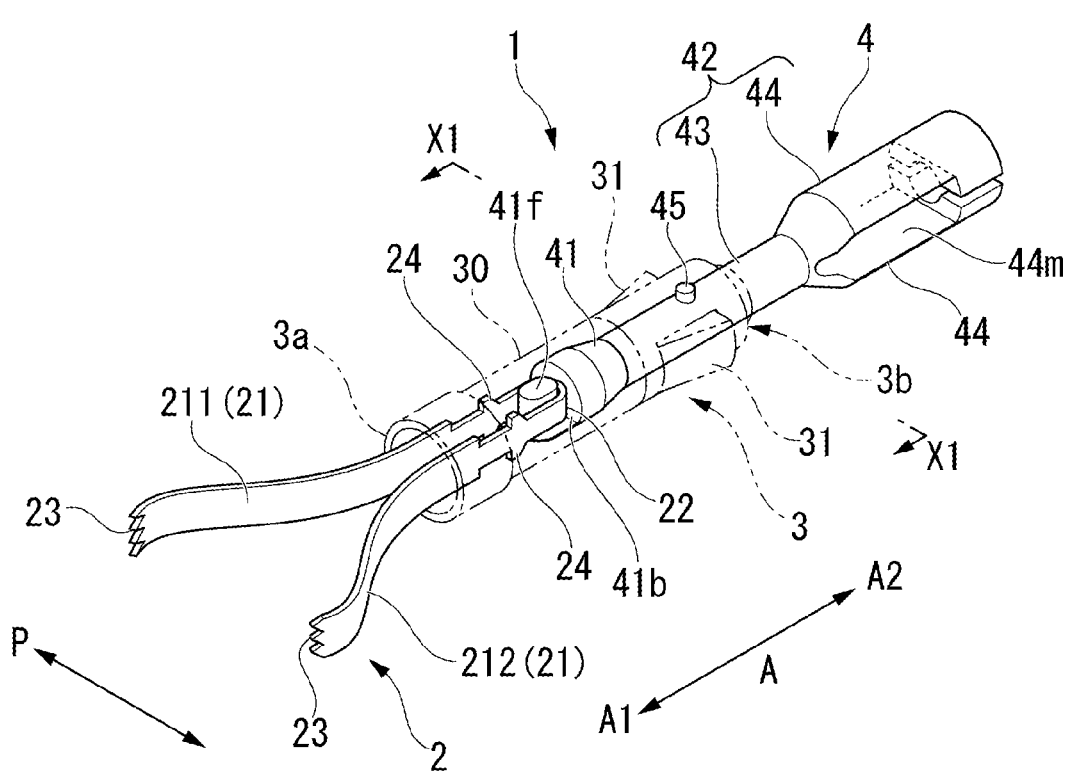
FIG. 3 is a perspective view of the clip unit transparently illustrating a presser tube.

FIG. 2 is a perspective view of the clip unit 1 of the cartridge system 100 according to this embodiment. FIG. 3 is a perspective view of the clip unit 1 transparently illustrating the presser tube 3. The clip unit 1 may include a clip 2, a presser tube (pipe) 3 serving, functioning, or acting as a fixing member, and a connection member (connector) 4. In the following description, the clip 2 side in a length direction A of the clip unit 1 is defined as a tip side (a distal side) A1 of the clip unit, and the connection member 4 side is defined as a base side (a proximal side) A2 of the clip unit 1.

The clip 2 may be formed, for example, by bending a metallic plate member such as a leaf spring member formed of a stainless steel material at a central portion thereof. The clip 2 may include a pair of arms 21 that can be opened and closed and a connection portion 22 that connects the pair of arms 21.

The pair of arms 21 may include a first arm 211 and a second arm 212. The first arm 211 and the second arm 212 may be disposed symmetric with respect to a center axis O1 in the length direction A of the clip unit 1. Tissue grasping portions 23 facing each other are formed at the tips of the pair of arms 21. The tissue grasping portions 23 may be formed such that the tips of the pair of arms 21 are bent inward.

An engagement portion 24 protruding in a direction perpendicular to the center axis O1 may be formed at the base end of the pair of arms 21. The tissue grasping portion 23 side of the engagement portion 24 may be formed as a slope with an acute angle, and the connection portion 22 side of the engagement portion 24 may be formed as a slope with an obtuse angle.

The connection portion 22 may be bent and formed in a U-shape and may be connected to the connection member 4. The connection portion 22 may be biased such that the pair of arms 21 is in an open state. Accordingly, the pair of arms 21 of the clip 2 can have a self-expanding force in an opening or closing direction P.

The presser tube 3 may include a presser tube body (pipe body) 30 formed in a tubular shape and a protruding or retracting wing 31. The presser tube body 30 may be formed by injection-molding a resin material with high rigidity. The presser tube body 30 may be formed of metal instead of a resin material with high rigidity. The protruding or retracting wing 31 may be formed by injection molding a material softer than the clip 2, for example, a resin material with high rigidity and with appropriate elasticity such as polyphthal-amide (PPA) or polyamide (PA).

The protruding or retracting wing 31 may be a pair of protrusions that protrudes and retracts with respect to an outer circumferential surface 30a of the presser tube body 30. The protruding or retracting wing 31 may be provided on both sides with the center axis O1 interposed therebetween. The protruding or retracting wing 31 can have a protruded state in which the protruding or retracting wing 31 protrudes outward in a radial direction from the outer circumferential surface 30a as a basic posture. The protruding or retracting wing 31 can be switched to a retracted state in which the protruding or retracting wing 31 retracts from the outer circumferential surface 30a with a force acting from the outside to the inside in the radial direction. By releasing the force, the protruding or retracting wing 31 can be returned from the retracted state to the protruded state.

The connection member 4 is connected to the connection portion 22 of the clip 2. The connection member 4 may be connected to the arrowhead-shaped hook portion 231 inserted into the sheath 220. That is, the connection member 4 may connect the clip 2 and the arrowhead-shaped hook portion 231. The connection member 4 may include an insertion portion 41 that can be inserted into an internal space of the presser tube 3, a connection portion 42 provided at a base end of the insertion portion 41, and an engagement protruding portion 45.

The insertion portion 41 may be an engagement portion that engages with (is connected to) the connection portion 22 of the clip 2. The insertion portion 41 may include a hook 41f provided on the tip side T1 and a breakable portion 41b provided on the base side A2 of the hook 41f. The hook 41f may extend in a direction perpendicular to the center axis O1 and may be formed in a substantially cylindrical rod shape. The connection portion 22 of the clip 2 may be hooked to the hook 41f.

The breakable portion 41b can be broken when a breaking force based on pulling of, for example, 20 N to 90 N is applied to the hook 41f and the connection portion 22 is pulled to the base side A2. The breakable portion 41b may include a mechanism for disconnecting the connection portion 22 of the clip 2 and the hook 41f of the connection member 4. For example, the breakable portion 41b may be a mechanism for disconnecting the connection portion 22 and the hook 41f through deformation without being broken (e.g., plastic deformation or elastic deformation).

The connection portion 42 may be an engagement portion that engages with (is connected to) the arrowhead-shaped hook portion 231 of the clip introduction device 200. The connection portion 42 may include a connection portion body 43 and a connection arm 44.

The connection arm 44 may be provided at a base end of the connection portion body 43 and may branch in a bifurcated shape. The connection arm 44 can be elastically deformed relative to the connection portion body 43 and can be opened and closed with respect to the connection portion body 43. A cutout portion 44m that can grasp and accommodate or store the engagement portion 231a of the arrowhead-shaped hook portion 231 may be formed in the connection arm 44. The cutout portion 44m may be formed in a shape which is in close contact with the outer circumferential surface of the engagement portion 231a of the arrowhead-shaped hook portion 231.

A direction D1 in which the connection arm 44 of the connection member 4 can be opened and closed is perpendicular to the opening or closing direction P of the pair of arms 21 when seen or viewed in the length direction A.

Figure 4:
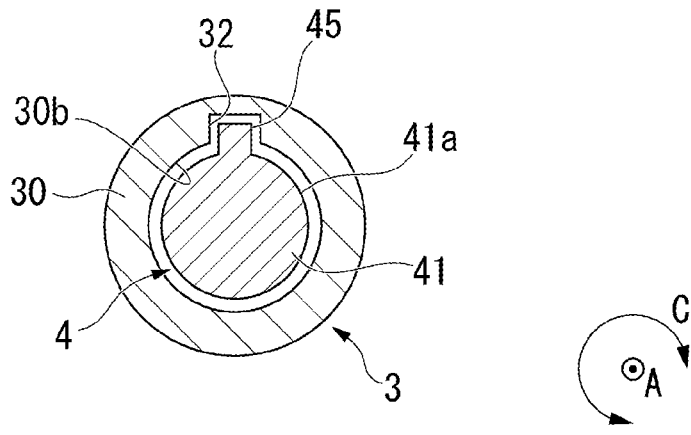
FIG. 4 is a sectional view of the clip unit taken along line X1-X1 in FIG. 3.

FIG. 4 is a sectional view of the clip unit 1 taken along line X1-X1 in FIG. 3. The engagement protruding portion 45 may be a protrusion protruding or extending outward from an outer circumferential surface 41a of the insertion portion 41. The engagement protruding portion 45 can engage with an engagement recessed portion 32 formed in the length direction A on an inner circumferential surface 30b of the presser tube body 30. Since the engagement protruding portion 45 and the engagement recessed portion 32 engage, connect, touch, contact, or the like with each other, the connection member 4 can move in the length direction A relative to the presser tube 3, but cannot rotate in a circumferential direction C relative to the presser tube 3.

A direction D2 in which the protruding or retracting wing 31 of the presser tube 3 protrudes and retracts is perpendicular to the direction D1 in which the connection arm 44 of the connection member 4 is opened and closed when seen in the length direction A. The direction D2 in which the protruding or retracting wing 31 of the presser tube 3 can protrude and retract can be different from the direction D1 in which the connection arm 44 of the connection member 4 is opened and closed when seen in the length direction A. An angle formed by the directions D1 and D2 may be close (or substantially close) to 90 degrees when seen or viewed in the length direction A.

Cartridge 5

Figure 5:
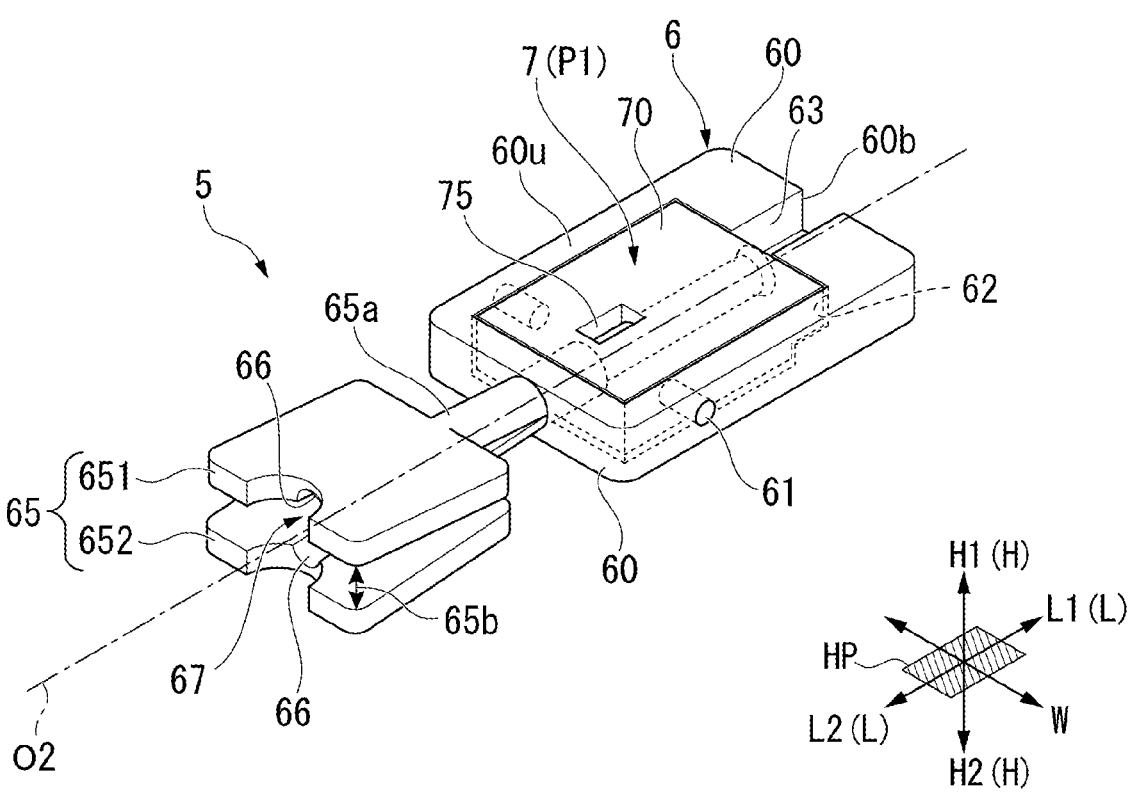
FIG. 5 is a perspective view of a cartridge of the cartridge system.
Figure 6:
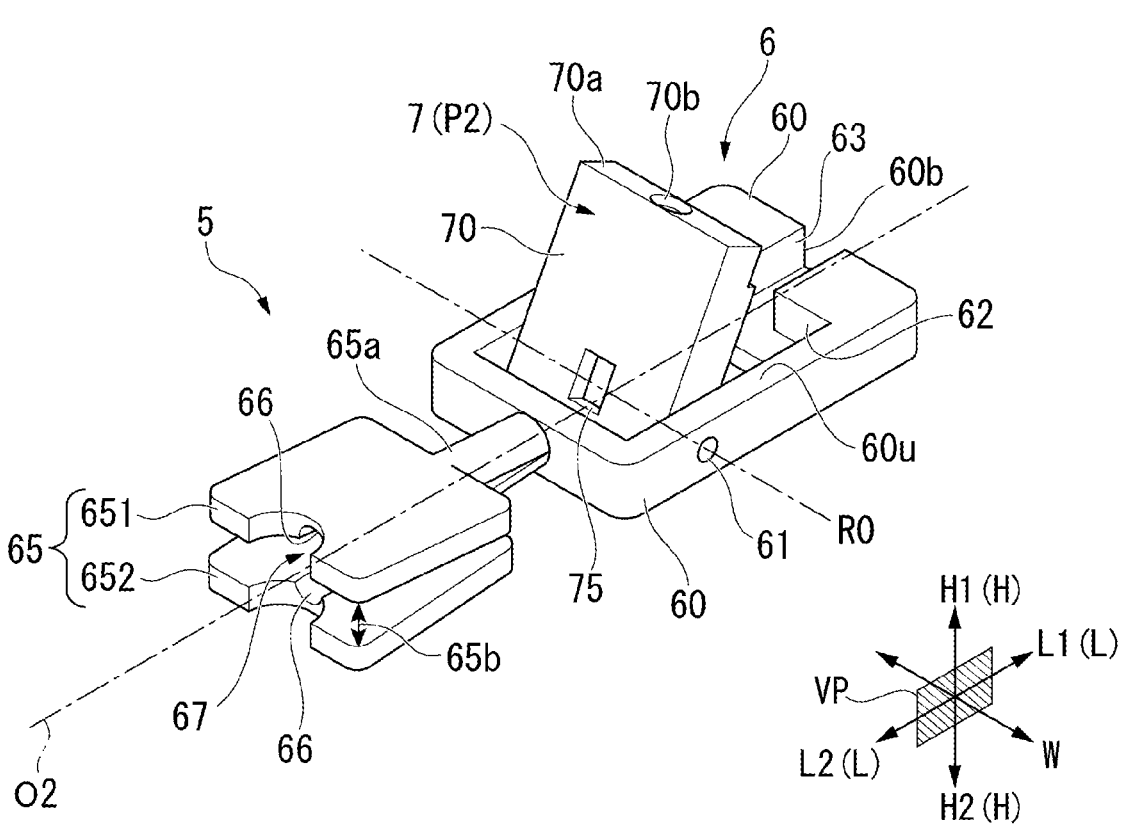
FIG. 6 is a perspective view of the cartridge.

FIGS. 5 and 6 are perspective views of the cartridge 5.

The cartridge 5 may be a case in which the clip unit 1 is stored. The width of the cartridge 5 may range from about 10 mm to 20 mm, the length may be about 50 mm, and the thickness may be about 5 mm, that is, the cartridge can be formed in an easy-to-hold size.

The cartridge 5 may be manufactured, for example, by injection-molding a transparent resin material with an appropriate hardness such as ABS, PC, PP, PS, acryl, or cycloolefin polymers. Since the cartridge 5 may be formed of a transparent resin material, a user can easily determine whether the clip unit 1 is present therein.

As illustrated in FIGS. 5 and 6, one of two directions perpendicular to the length direction L of the cartridge 5 and perpendicular to each other is defined as a "width direction W," and the other is defined as a "height direction H." A plane parallel to the length direction L and the width direction W is defined as a "horizontal plane HP," and a plane parallel to the length direction L and the height direction H is defined as a "vertical plane VP." In the cartridge 5 in which the clip unit 1 is stored, the pair of arms 21 side is defined as a tip side L1 of the cartridge 5, and the connection member 4 side is defined as a base side L2 of the cartridge 5.

Figure 7:
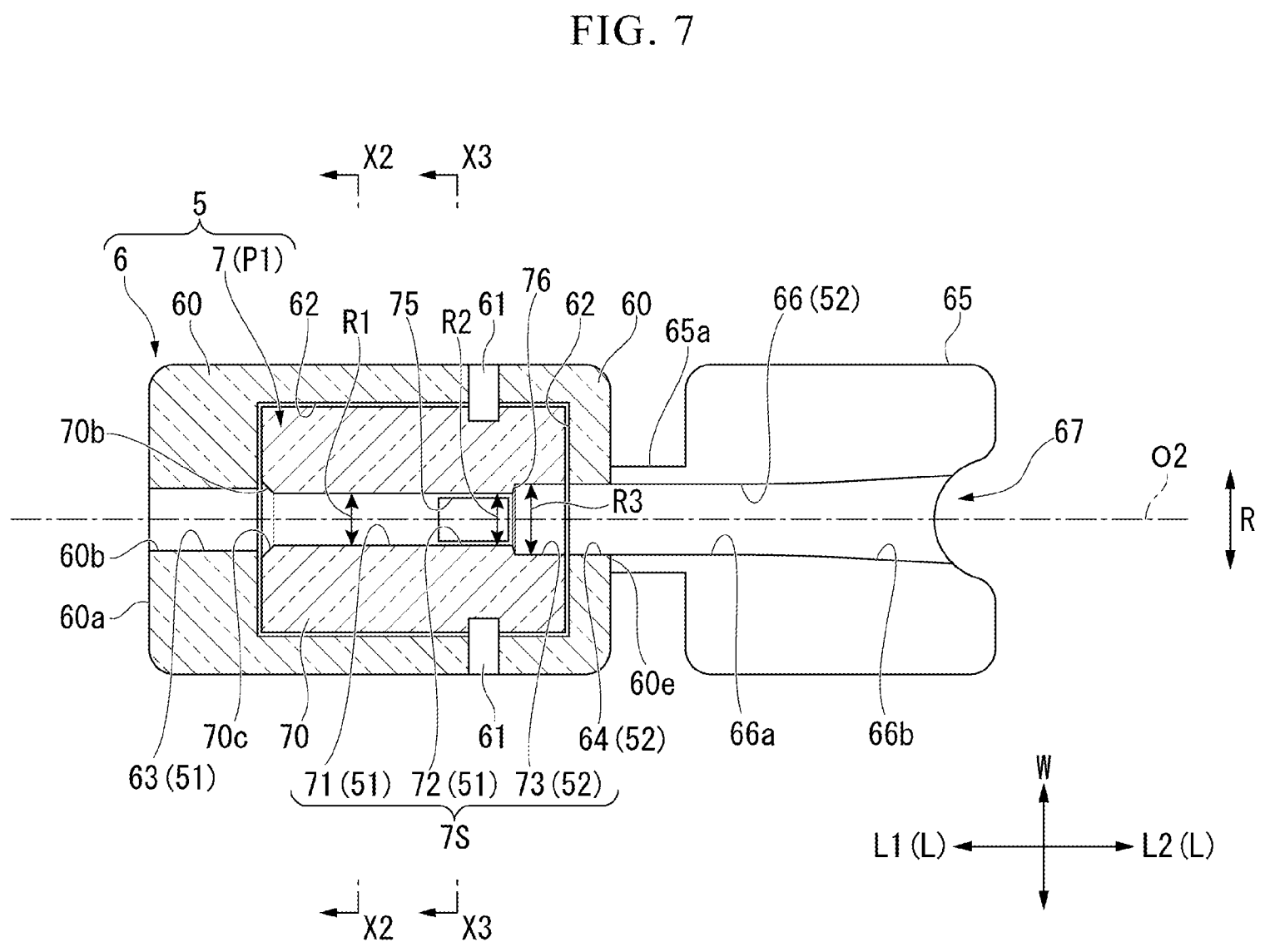

FIG. 7 is a sectional view of the cartridge 5.

The cartridge 5 may include a first cartridge 6 and a second cartridge 7. The first cartridge 6 can accommodate the second cartridge 7 as illustrated in FIG. 5. The second cartridge 7 can be rotatably attached to the first cartridge 6 as illustrated in FIG. 6.

The first cartridge 6 may include a cartridge outer circumferential portion 60, a compression portion 65, and a sheath connection portion 66.

The cartridge outer circumferential portion 60 may be formed in a substantially rectangular box shape. A length in the width direction W of the cartridge outer circumferential portion 60 may be greater than a length in the height direction H of the cartridge outer circumferential portion 60. The cartridge outer circumferential portion 60 may include a second cartridge support portion 61, a second cartridge accommodation portion 62, an arm accommodation portion 63, and a sheath insertion portion 64.

As illustrated in FIG. 6, the second cartridge support portion 61 may support the second cartridge 7 to be rotatable about a rotation axis RO extending in the width direction W relative to the cartridge outer circumferential portion 60.

The second cartridge accommodation portion 62 may be a recessed portion formed in a top surface 60u of the cartridge outer circumferential portion 60 and open to the top side H1 in the height direction H. The second cartridge accommodation portion 62 may be formed in a substantially rectangular shape when seen or viewed in the height direction H. As illustrated in FIG. 5, the second cartridge 7 can be accommodated in the second cartridge accommodation portion 62.

The arm accommodation portion 63 may be a recessed portion formed in the top surface 60u of the cartridge outer circumferential portion 60 and opened to the top side H1 in the height direction H. As illustrated in FIG. 6, the arm accommodation portion 63 may communicate with, touch, connect, contact, or the like a tip opening 60b formed at the tip 60a of the cartridge outer circumferential portion 60 on the tip side L1. The arm accommodation portion 63 may communicate with, touch, connect, contact, or the like the second cartridge accommodation portion 62 on the base side L2.

The sheath insertion portion 64 may be a through-hole into which the sheath 220 can be inserted and which is provided on the base side L2 of the second cartridge accommodation portion 62. The sheath insertion portion 64 may penetrate from the second cartridge accommodation portion 62 to a base end 60e of the cartridge outer circumferential portion 60.

The compression portion 65 may be a plate-shaped member provided at the base end 60e of the cartridge outer circumferential portion 60. The compression portion 65 may include a first compression portion 651 and a second compression portion 652. The first compression portion 651 and the second compression portion 652 may be provided or located so as to face each other in the height direction H of the cartridge 5.

The compression portion 65 may include a connection portion 65a connected to the cartridge outer circumferential portion 60. The connection portion 65a may separately connect the first compression portion 651 and the second compression portion 652 to the cartridge outer circumferential portion 60. The connection portion 65a can be bent such that the first compression portion 651 and the second compression portion 652 get, move, or are located far away from each other. Accordingly, a gap 65b can be formed between the first compression portion 651 and the second compression portion 652. The first compression portion 651 and the second compression portion 652 may be, may get, may move, or the like farther away on the base side L2 than on the tip side L1.

The sheath connection portion 66 may be an insertion groove into which the sheath 220 can be inserted. The sheath connection portion 66 may be an arc-shaped groove formed in the inner surfaces of the first compression portion 651 and the second compression portion 652. The sheath connection portion 66 may communicate with, touch, connect, contact, or the like the second cartridge accommodation portion 62 of the cartridge outer circumferential portion 60 via the sheath insertion portion 64. The sheath connection portion 66 may include a straight portion 66a with a diameter not changed and a tapered portion 66b with a diameter increasing gradually toward an insertion port 67 on the base side L2.

A user can fix the sheath 220 to the first cartridge 6 by compressing the first compression portion 651 and the second compression portion 652 in a state in which the sheath 220 can be inserted into the sheath connection portion 66 via the insertion port 67.

The second cartridge 7 may be formed in a substantially rectangular box shape and can be accommodated in the second cartridge accommodation portion 62. The second cartridge 7 may be supported to be rotatable about the rotation axis RO extending in the width direction W relative to the cartridge outer circumferential portion 60. Specifically, the second cartridge 7 can move between a first position P1 (FIG. 5) and a second position P2 (FIG. 6). The first position P1 is a position of the second cartridge 7 at which the second cartridge 7 can be accommodated or stored in the second cartridge accommodation portion 62. The second position P2 may be a position of the second cartridge 7 at which the tip 70a which is an end on the tip side L1 of the second cartridge 7 has rotated to the vicinity of the top side H1 of the second cartridge accommodation portion 62.

The second cartridge 7 may include a cartridge body 70 formed in a substantially rectangular box shape and a storage area 7S formed in the cartridge body 70.

FIG. 8 is a sectional view of the cartridge 5 in which the clip unit 1 is stored.

The cartridge body 70 may include a clip unit insertion port 70b communicating with, touching, connecting with, or the like the storage area 7S at the tip 70a as illustrated in FIG. 7. A user can store the clip unit 1 in the cartridge 5 by inserting the clip unit 1 from the base side A2 into the clip unit insertion port 70b. When the second cartridge 7 is located at the first position P1, the clip unit insertion port 70b communicates with, touches, contacts, or the like the arm accommodation portion 63 of the first cartridge 6. When the second cartridge 7 is located at the second position P2, the clip unit insertion port 70b can be separated from the first cartridge 6.

The storage area 7S is a path penetrating the cartridge body 70 and is an internal space in which at least a part of the clip unit 1 is stored to be movable in the length direction L. The storage area 7S is a path which extends in the length direction L of the cartridge 5, communicates with the arm accommodation portion 63 on the tip side L1, and communicates with, touches, contacts, or the like the sheath connection portion 66 on the base side L2 when the second cartridge 7 is located at the first position P1 as illustrated in FIG. 7.

The storage area 7S may include a first area 71, a second area 72, and a sheath insertion area 73. The first area 71, the second area 72, and the sheath insertion area 73 may be arranged from the tip side L1 to the base side L2 in the length direction L. In this embodiment, the storage area 7S can be an area passing through the center axis O2 in the length direction L of the cartridge 5 and can be an internal space that is formed symmetric with respect to the horizontal plane HP including the center axis O2.

Figure 9:
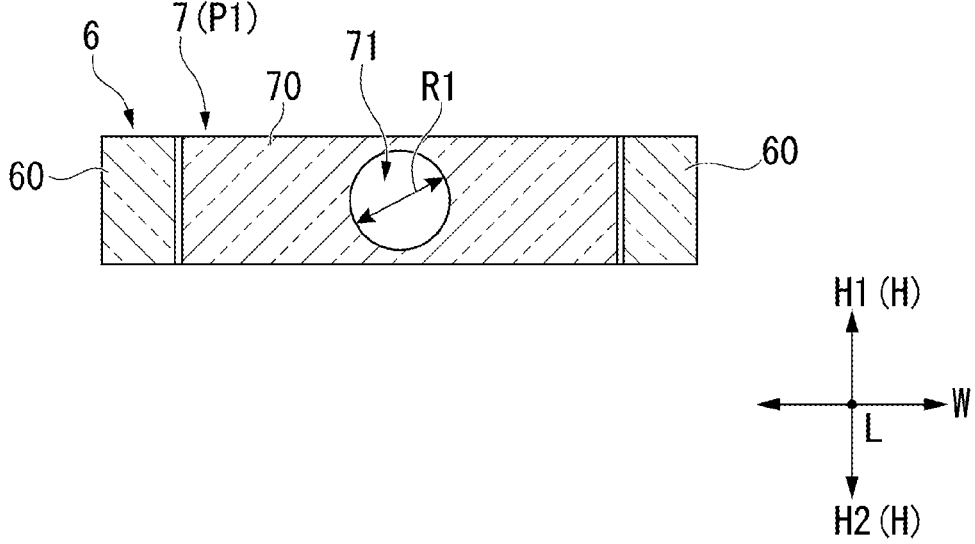
FIG. 9 is a sectional view of a first area taken along line X2-X2 in FIG. 7.

FIG. 9 is a sectional view of the first area 71 taken along line X2-X2 in FIG. 7.

The first area 71 may form a hollow area of which a sectional surface perpendicular to the length direction (moving direction) L has a circular shape. The first area 71 may be located on the tip side L1 of the second area 72 and may communicate with, connect with, contact, touch, or the like, the clip unit insertion port 70b on the tip side L1. The first area 71 can communicate with the arm accommodation portion 63 when the second cartridge is located at the first position P1.

The first area 71 may include a tapered portion 70c formed in a taper shape on the base side L2 of the clip unit insertion port 70b. The tapered portion 70c may decrease in diameter from the tip side L1 to the base side L2.

The first area 71 may be an area in which the protruding or retracting wing 31 is maintained in a retracted state in which it can be accommodated or stored in the sheath 220. An inner radius R1 of the first area 71 may be slightly larger than an outer diameter of the presser tube 3, and the inner circumferential surface of the first area 71 can push the protruding or retracting wing 31 inward until the protruding or retracting wing 31 becomes or enters the retracted state. When the clip unit 1 is inserted into the first area 71, the protruding or retracting wing 31 of the presser tube 3 can be gradually pushed inward to be in the retracted state by the tapered portion 70c.

The first area 71 is an area in which the connection arm 44 of the connection member 4 can be enlarged in a radial direction R and can be prohibited from becoming an open state in which it is connectable to the arrowhead-shaped hook portion 231 of the applicator 200 (e.g., an area in which transition to the open state is not possible).

Figure 10:
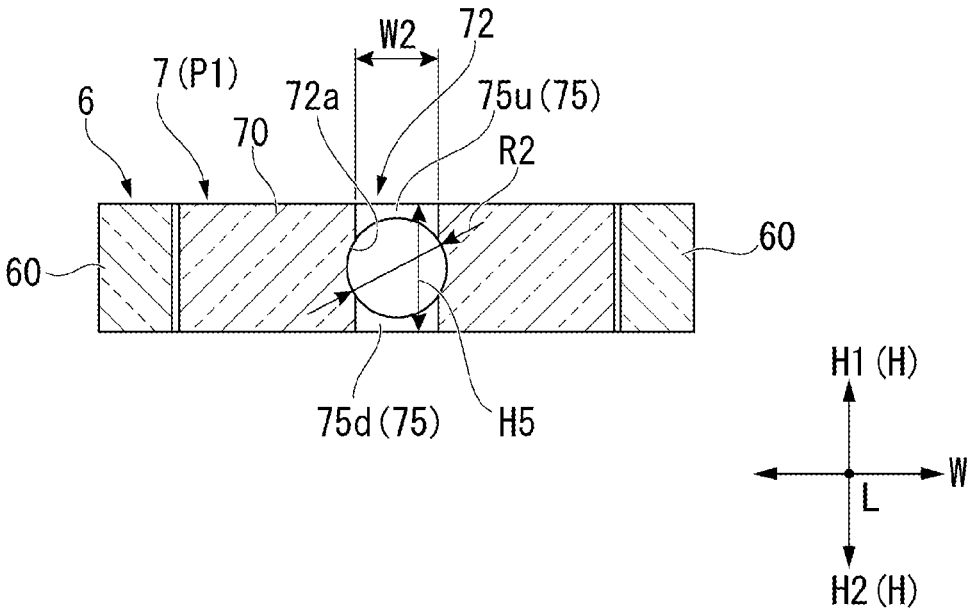
FIG. 10 is a sectional view of a second area taken along line X3-X3 in FIG. 7.

FIG. 10 is a sectional view of the second area 72 taken along line X3-X3 in FIG. 7.

The second area 72 may form a hollow area of which a sectional surface perpendicular to the length direction (moving direction) L has a circular shape. The second area 72 may be located on the base side L2 of the first area 71 and may be located on the tip side L1 of the sheath insertion area 73. An inner radial R2 of the second area 72 may be equal to the inner radius R1 of the first area 71.

In the second area 72, a pair of recessed portion areas 75 (an upper recessed portion area 75u and a lower recessed portion area 75d) that are recessed outward in the radial direction R may be formed on the top side H1 and the bottom side H2 in the height direction H. In this embodiment, the pair of recessed portion areas 75 (the upper recessed portion area 75u and the lower recessed portion area 75d) may be through-holes (e.g., windows or openings) penetrating the cartridge body 70.

The second area 72 may be an area in which the connection arm 44 of the connection member 4 can be elastically enlarged in the radial direction R and can be permitted to become the open state in which it can be connected to the arrowhead-shaped hook portion 231 of the applicator 200 (e.g., an area in which transition to the open state is possible). A length H5 in the height direction H of the hollow area of the second area 72 in which the pair of recessed portion areas 75 are formed may be much larger than the inner radius R2. The length H5 may be larger than a maximum length H4 in the height direction H of the connection arm 44 in the open state (see FIG. 21). Accordingly, the connection arm 44 disposed in the second area 72 in which the pair of recessed portion areas 75 are formed can be opened in the height direction H (elastically enlarged) until the arrowhead-shaped hook portion 231 can be inserted into the gap of the connection arm 44.

The sheath insertion area 73 may form a hollow area of which a sectional surface perpendicular to the length direction (moving direction) L has a circular shape. The sheath insertion area 73 may be located on the base side L2 of the second area 72. An inner radius R3 of the sheath insertion area 73 may be larger than the inner radius R2 of the second area 72. The sheath insertion area 73 may communicate with, touch, contact, or the like the sheath connection portion 66 via the sheath insertion portion 64 when the second cartridge 7 is located at the first position P1.

The sheath insertion area 73 may be an area into which a tip of the sheath 220 passing through the sheath connection portion 66 can be inserted. A sheath contact portion 76 with which the distal tip 221 of the inserted sheath 220 can come into contact is formed in the sheath insertion area 73.

When the second cartridge 7 is located at the first position P1, the arm accommodation portion 63 of the first cartridge 6 and the first area 71 and the second area 72 of the cartridge body 70 of the second cartridge 7 can form a first path 51 (also referred to as a clip unit path 51 of the cartridge 5) extending in the length direction L.

When the second cartridge 7 is located at the first position P1, the sheath connection portion 66 and the sheath insertion portion 64 of the first cartridge 6 and the sheath insertion area 73 of the cartridge body 70 of the second cartridge 7 can form a second path 52 (also referred to as a sheath path 52 of the cartridge 5) extending in the length direction L.

The first path 51 and the second path 52 can form a continuous space extending in the length direction L of the cartridge 5.

Method of Loading Clip Unit 1

The operations of the cartridge system 100 will be described below. FIGS. 11 to 25 are diagrams illustrating a method of loading the clip unit 1 into the clip introduction device 200 using the cartridge 5.

Figure 11:
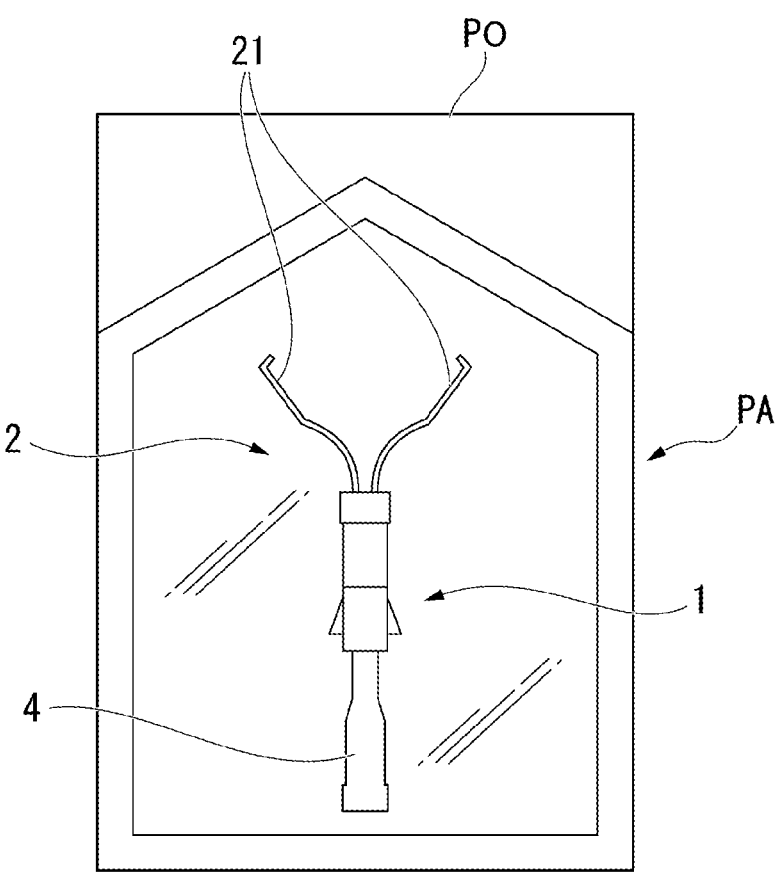
FIG. 11 is a diagram illustrating the clip unit enclosed in a sterilized pack.

FIG. 11 is a diagram illustrating the clip unit 1 enclosed in a sterilized pack PA.

The clip unit 1 may be enclosed in a sterilized pack PA such that the clip 2 of the clip unit 1 can be directed to an unsealing opening PO of the sterilized pack PA. A user can open the unsealing opening PO of the sterilized pack PA and take out or remove the clip unit 1.

Figure 12:
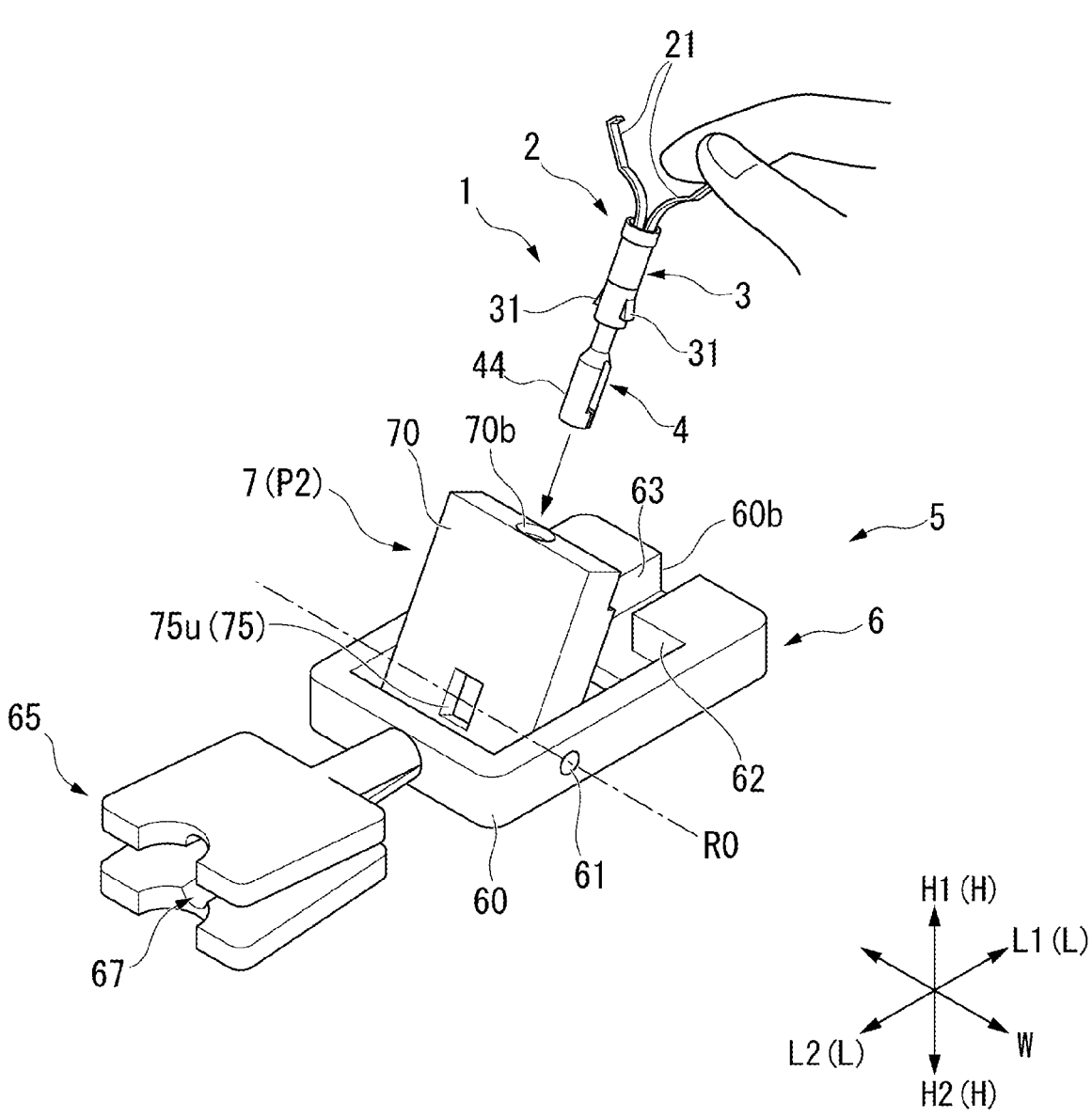
FIG. 12 is a diagram illustrating the clip unit which is inserted into the cartridge.

FIG. 12 is a diagram illustrating the clip unit 1 which is inserted into the cartridge 5 (the second cartridge 7). A user can rotate the second cartridge 7 and locate the second cartridge 7 at the second position P2. The user can hold a pair of arms 21 of the clip unit 1 taken out of the sterilized pack PA with fingers, insert the clip unit 1 into the clip unit insertion port 70b from the base side A2, and store the clip unit 1 in the storage area 7S of the second cartridge 7. Although rubber gloves are not illustrated in FIG. 12 and the like, the user can hold the cartridge 5 and the clip unit 1 in a state in which the rubber gloves are worn on the hands.

Figure 13:
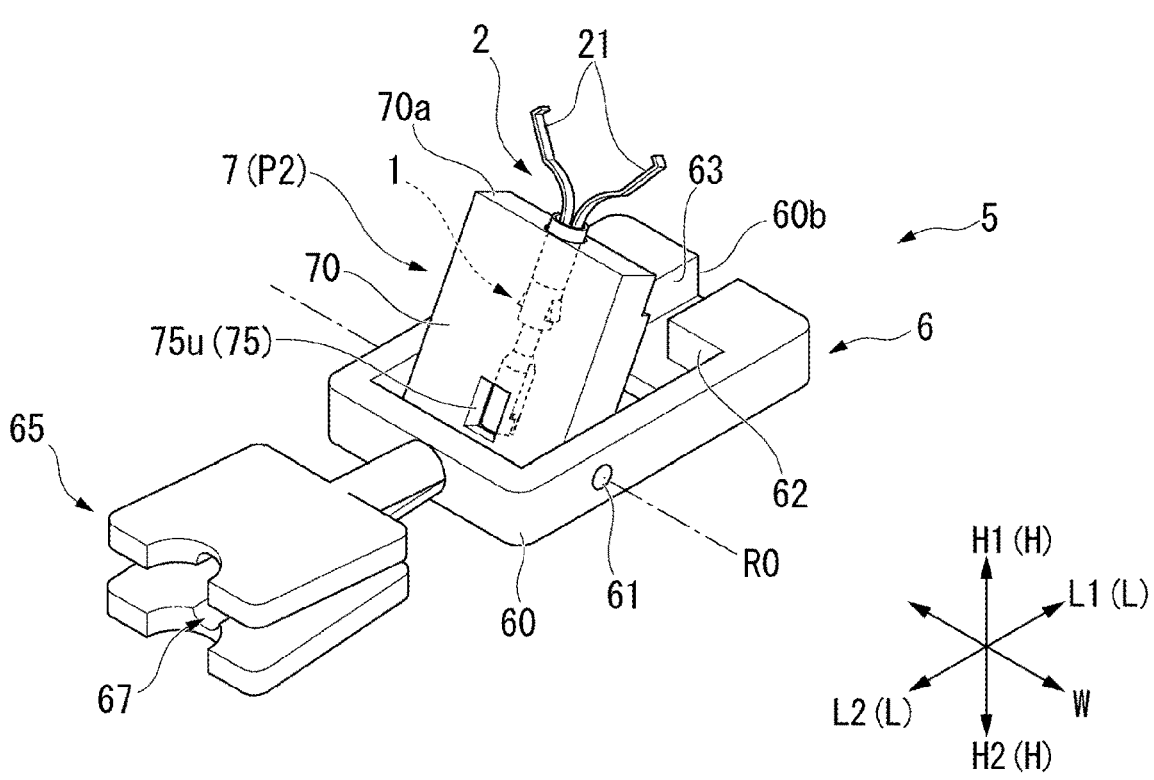
FIG. 13 is a diagram illustrating the clip unit stored in the cartridge.

FIG. 13 is a diagram illustrating the clip unit 1 inserted into the cartridge 5 (the second cartridge 7). The user can push the clip unit 1 into the storage area 7S of the second cartridge 7. The protruding or retracting wing 31 of the clip unit 1 can be pushed inward until the protruding or retracting wing 31 becomes or enters a retracted state by the inner circumferential surface of the first area 71. The user can push the clip unit 1 until the connection arm 44 of the connection member 4 of the clip unit 1 can be located in the second area 72. That is, at least a part of the clip unit 1 can be stored in the second cartridge 7.

Figure 14:
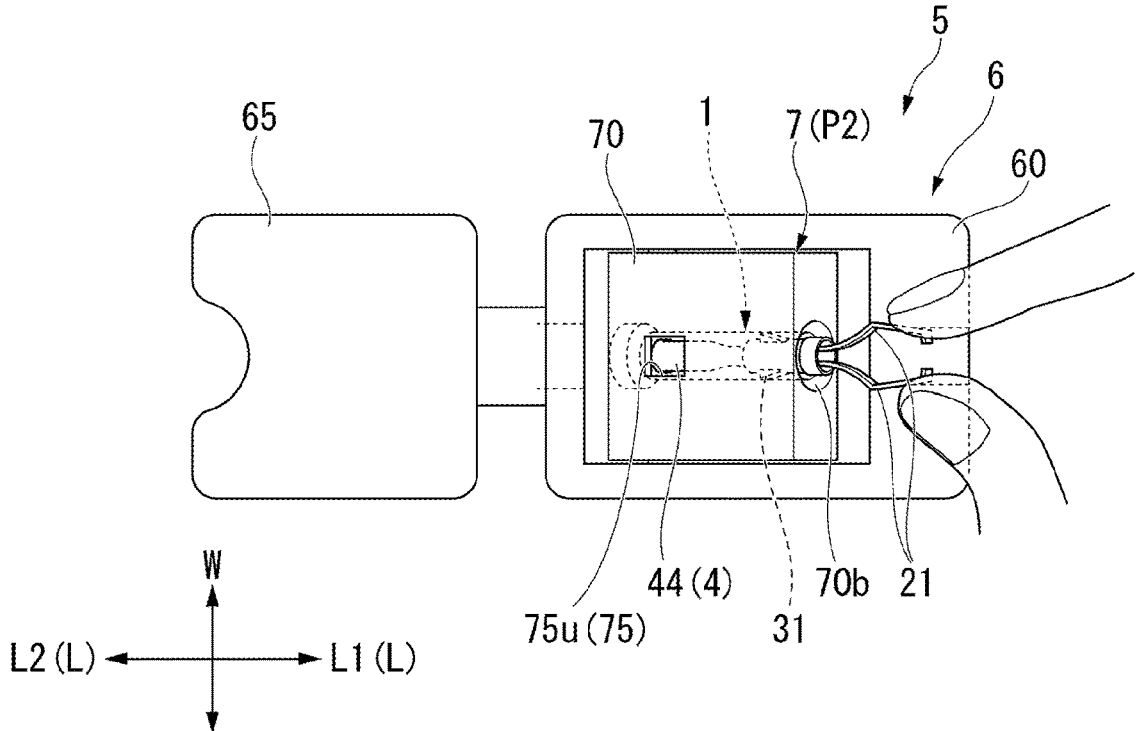
FIG. 14 is a diagram illustrating a second cartridge which is accommodated in a first cartridge in the cartridge.

FIG. 14 is a diagram illustrating the second cartridge 7 and the clip unit 1 which are accommodated in the first cartridge 6. A user can close a pair of arms 21 of the clip unit 1 with fingers, rotate the second cartridge 7, and accommodate or store the second cartridge 7 at the first position P1.

Figure 15:
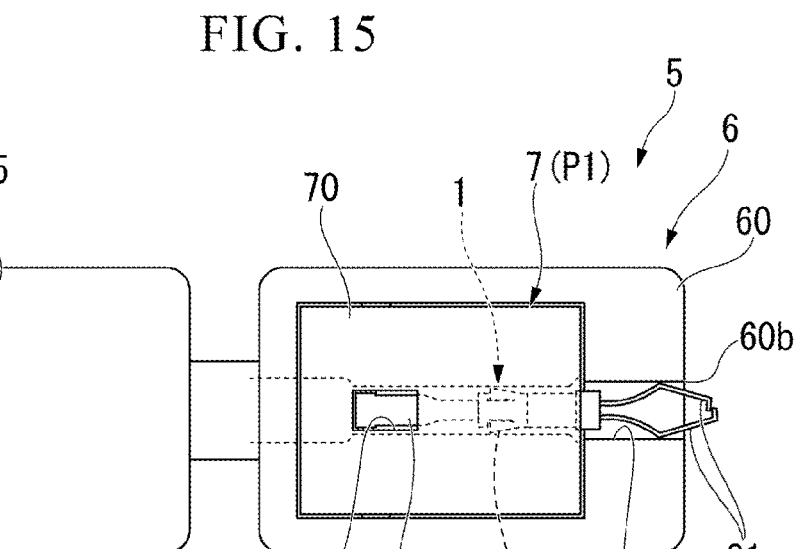
FIG. 15 is a diagram illustrating the second cartridge accommodated in the first cartridge.

FIG. 15 is a diagram illustrating the second cartridge 7 and the clip unit 1 accommodated in the first cartridge 6. A user can close a pair of arms 21 of the clip unit 1 with fingers and accommodate or store the pair of arms 21 of the clip unit 1 in the arm accommodation portion 63 of the first cartridge 6. The pair of arms 21 can be accommodated or stored in the arm accommodation portion 63 such that the opening or closing direction P of the pair of arms 21 can match the width direction W. The clip unit 1 may be stored in the first path 51 (the arm accommodation portion 63, the first area 71, and the second area 72).

Figure 16:
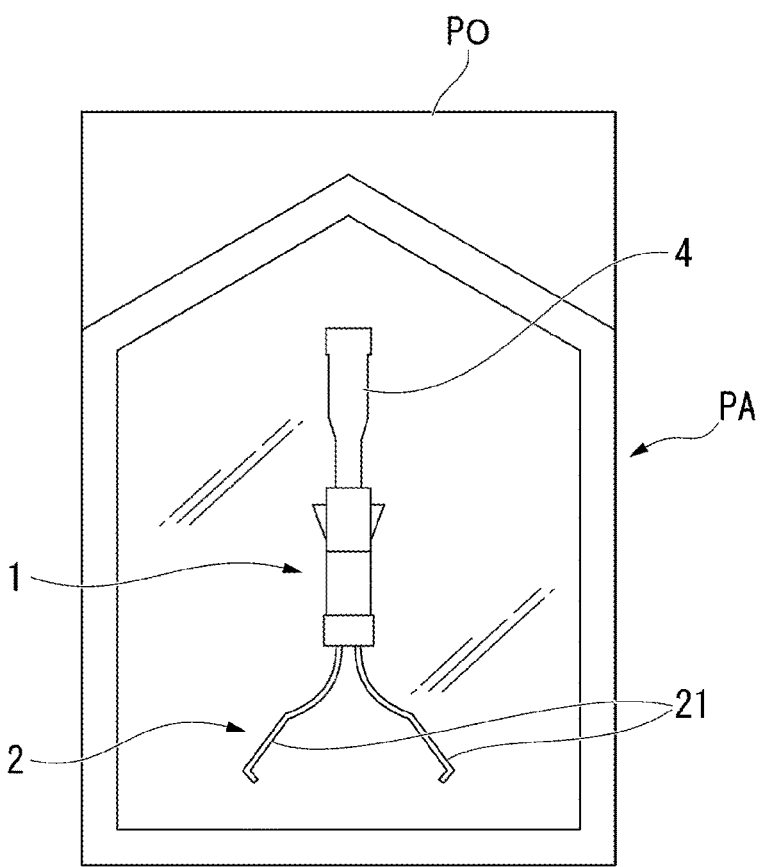
FIG. 16 is a diagram illustrating the clip unit enclosed in the sterilized pack.

FIG. 16 is a diagram illustrating the clip unit 1 enclosed in a sterilized pack PA.

The clip unit 1 may be enclosed in the sterilized pack PA such that the connection member 4 of the clip unit 1 faces the unsealing opening PO of the sterilized pack PA.

Figure 17:
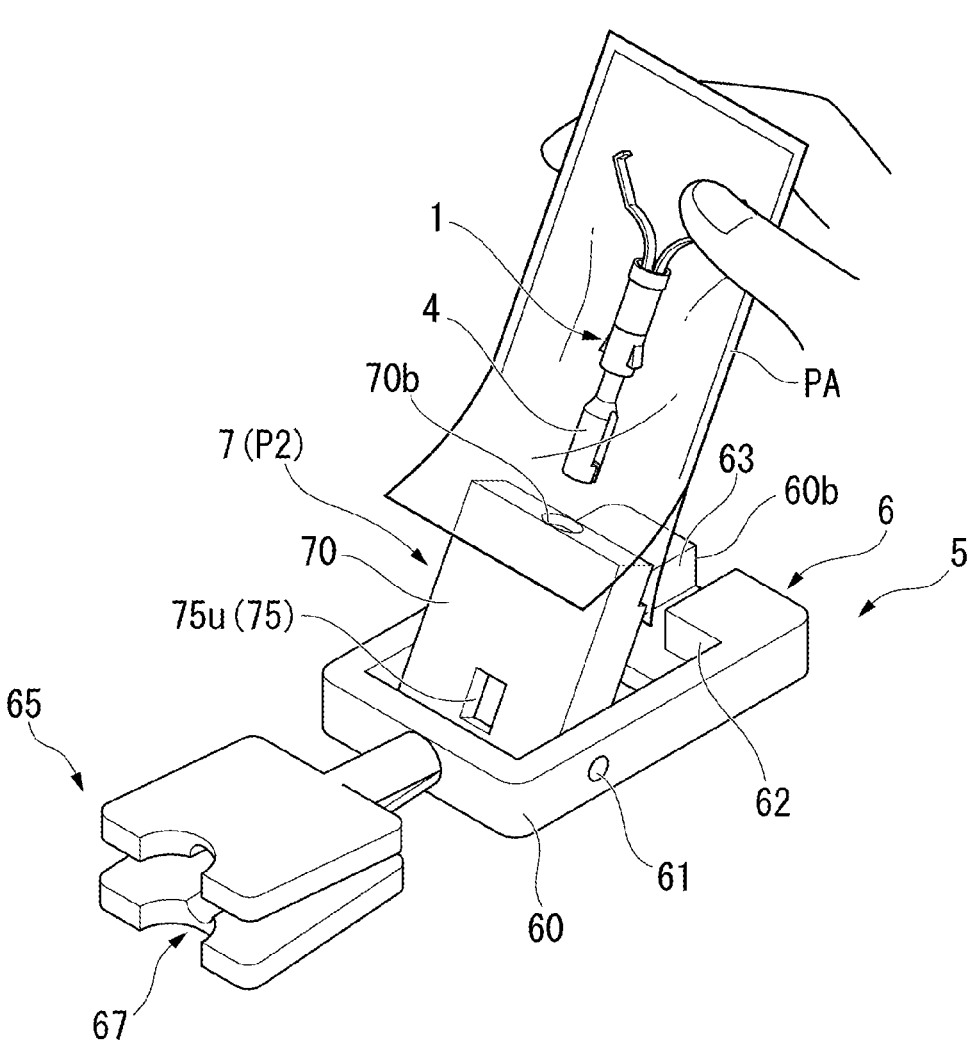
FIG. 17 is a diagram illustrating the clip unit which is inserted into the cartridge.

FIG. 17 is a diagram illustrating the clip unit 1 which is inserted into the cartridge 5.

The clip unit 1 enclosed as illustrated in FIG. 16 can be stored in the storage area 7S of the second cartridge 7 by opening the unsealing opening PO of the sterilized pack PA and then inserting the clip unit 1 into the clip unit insertion port 70*b*. The user can store the clip unit 1 in the storage area 7S without taking out the clip unit 1 from the sterilized pack PA.

Figure 18:
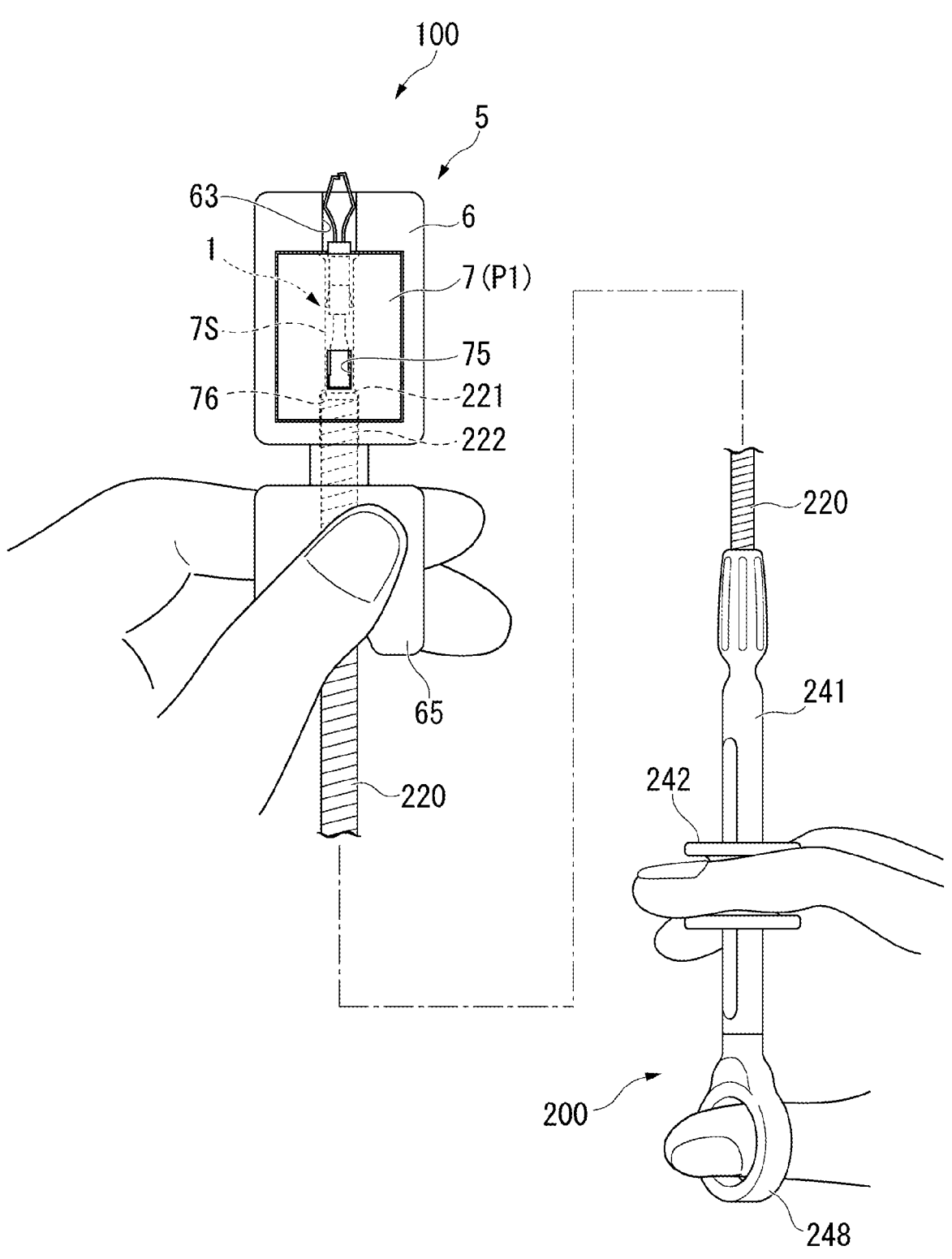
FIG. 18 is a diagram illustrating an operation of loading the clip unit.

FIG. 18 is a diagram illustrating an operation of loading the clip unit 1.

A user can insert the sheath 220 into the second path 52 (the sheath connection portion 66, the sheath insertion portion 64, and the sheath insertion area 73) via the insertion port 67 and bring the distal tip 221 of the sheath 220 into contact with the sheath contact portion 76 of the sheath insertion area 73. The user can fix the sheath 220 to the first cartridge 6 by compressing the sheath 220 with the compression portion 65.

Figure 19:
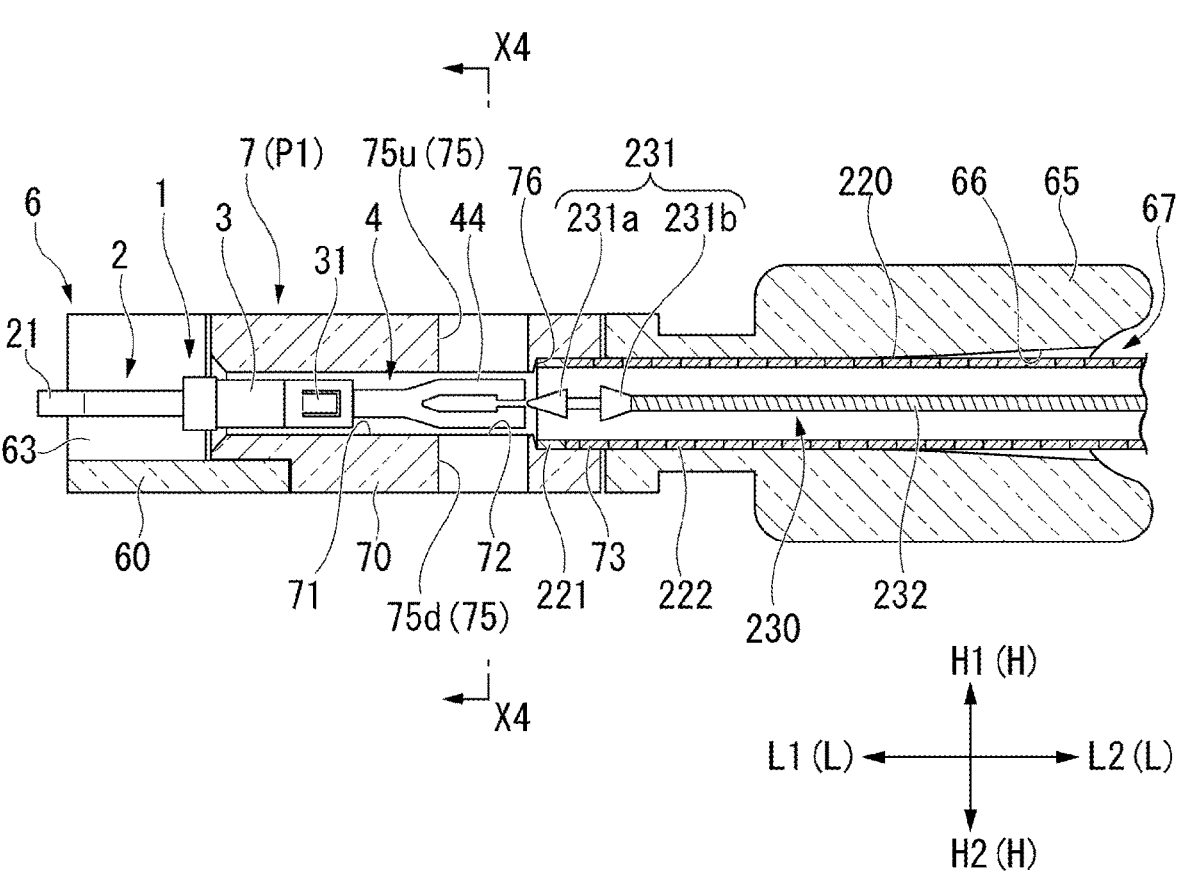
FIG. 19 is a diagram illustrating the clip unit which is connected to the clip introduction device.

FIG. 19 is a diagram illustrating the clip unit 1 which is connected to the clip introduction device 200.

A user can cause the arrowhead-shaped hook portion 231 to approach the connection member 4 by moving the slider 242 relative to the operation portion body 241 of the operation portion 240 and moving the operating wire 230 relative to the sheath 220.

Figure 20:
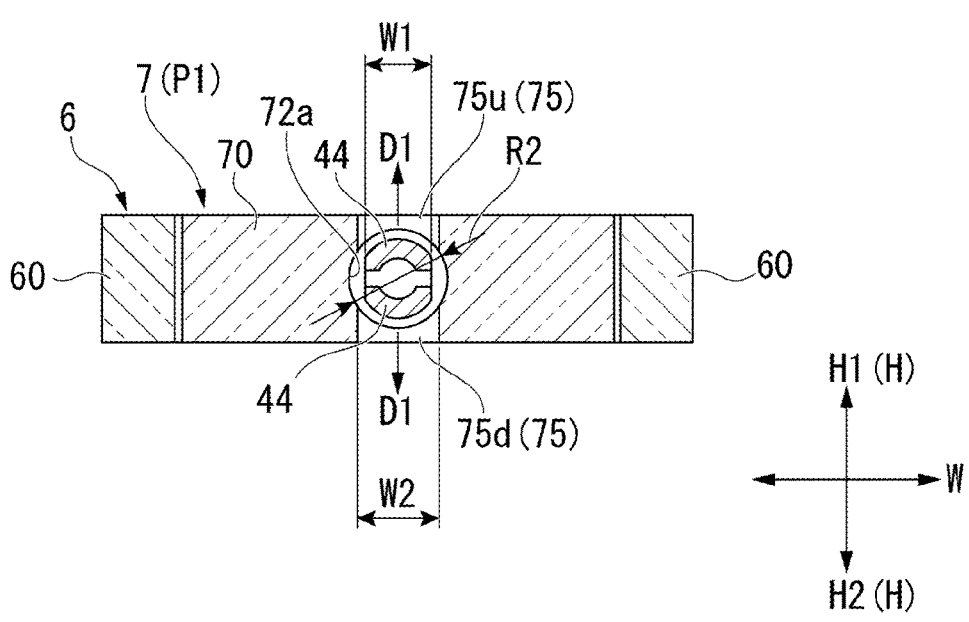
FIG. 20 is a sectional view of the second area taken along line X4-X4 in FIG. 19.

FIG. 20 is a sectional view of the second area 72 taken along line X4-X4 in FIG. 19.

The clip unit 1 may be stored in the storage area 7S such that the opening or closing direction P of a pair of arms 21 matches the width direction W. Accordingly, the direction D1 in which the connection arm 44 of the connection member 4 is opened and closed may be parallel to the height direction H in which a pair of recessed portion areas 75 are formed in the second area 72. A width W1 in the width direction W of the connection arm 44 may be smaller than a width W2 in the width direction W of the pair of recessed portion areas 75. Accordingly, the connection arm 44 disposed in the second area 72 in which the pair of recessed portion areas 75 are formed can open (be elastically enlarged) in the height direction H until the arrowhead-shaped hook portion 231 can be inserted into the gap in the connection arm 44.

Figure 21:
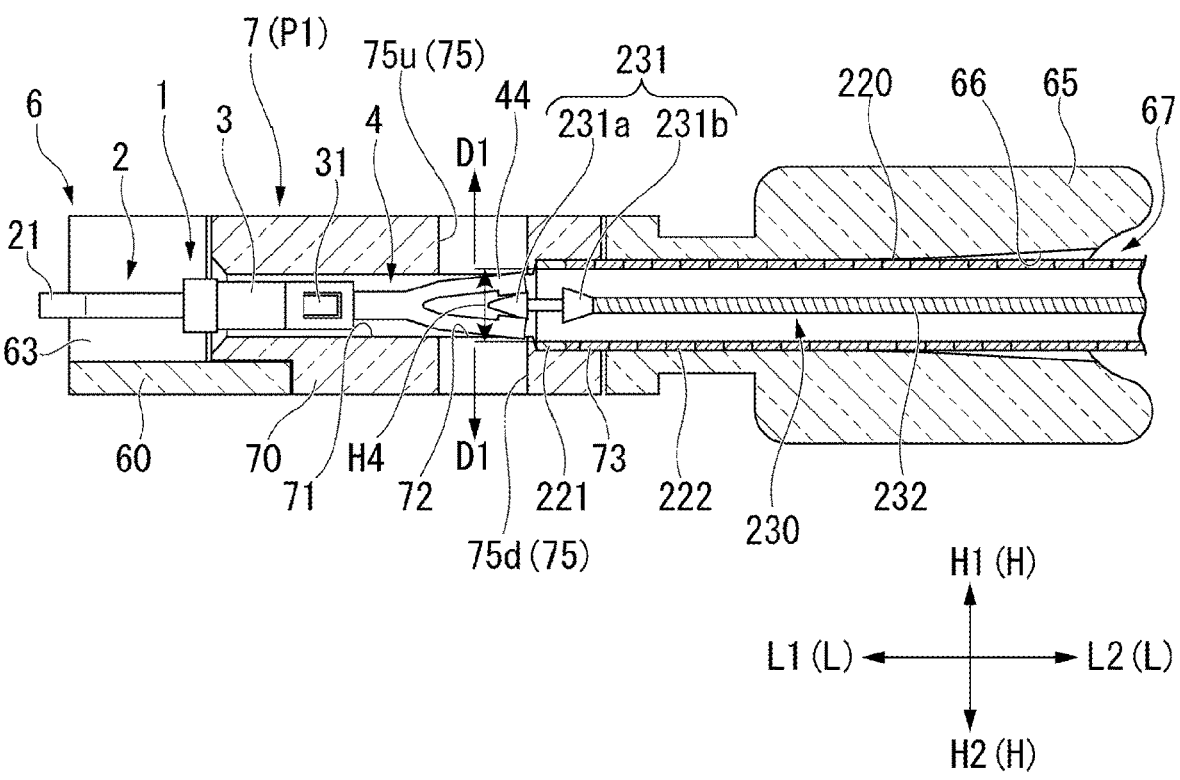
FIG. 21 is a diagram illustrating the clip unit which is connected to the clip introduction device.

FIG. 21 is a diagram illustrating the clip unit 1 which is connected to the clip introduction device 200.

A user can move the slider 242 relative to the operation portion body 241 of the operation portion 240 to insert the arrowhead-shaped hook portion 231 into the connection member 4. In such an example, the clip unit 1 does not move forward in the length direction (moving direction) L due to a frictional force generated between the closed arms 21 and the arm accommodation portion 63. The connection arm 44 engaging with the engagement portion 231*a* of the arrowhead-shaped hook portion 231 can be enlarged in the direction D1.

Figure 22:
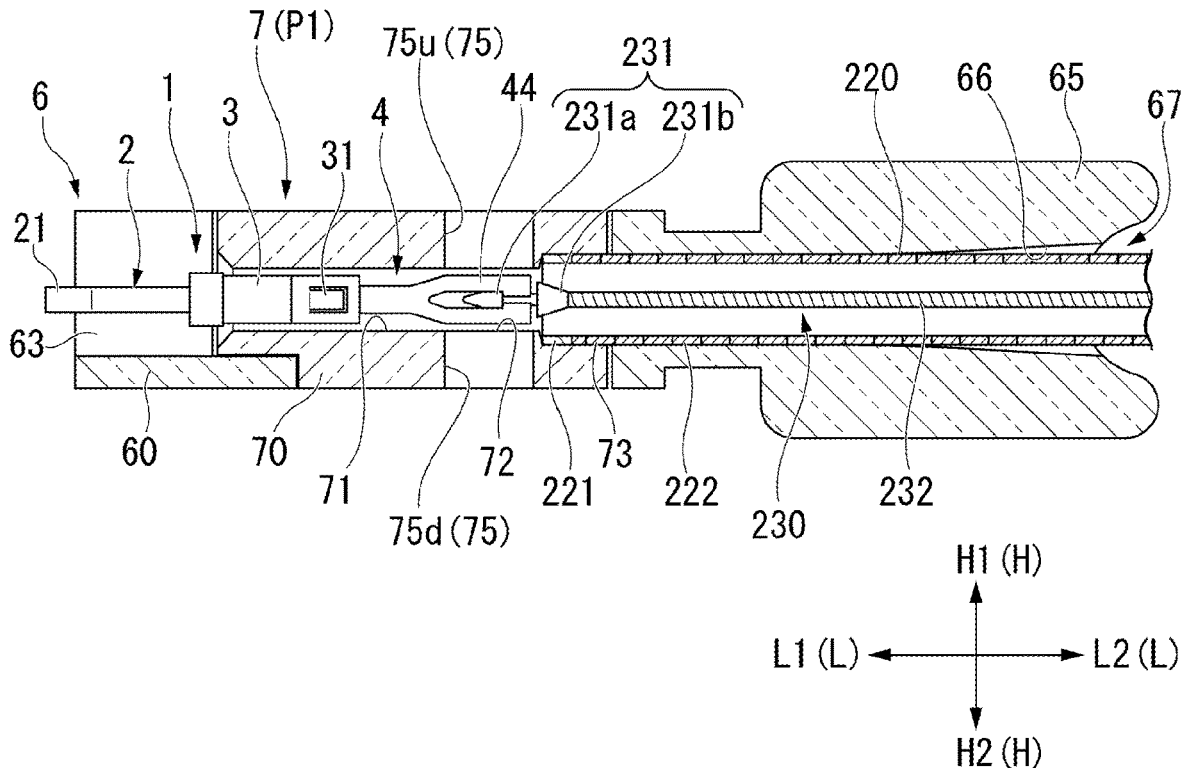
FIG. 22 is a diagram illustrating the clip unit connected to the clip introduction device.

FIG. 22 is a diagram illustrating the clip unit 1 connected to the clip introduction device 200.

A user can further move the slider 242 relative to the operation portion body 241 of the operation portion 240. The engagement portion 231*a* of the arrowhead-shaped hook portion 231 can be received in the cutout portion 44*m*, and the connection arm 44 can be closed. As a result, the arrowhead-shaped hook portion 231 can be connected to the connection member 4 of the clip unit 1.

Figure 23:
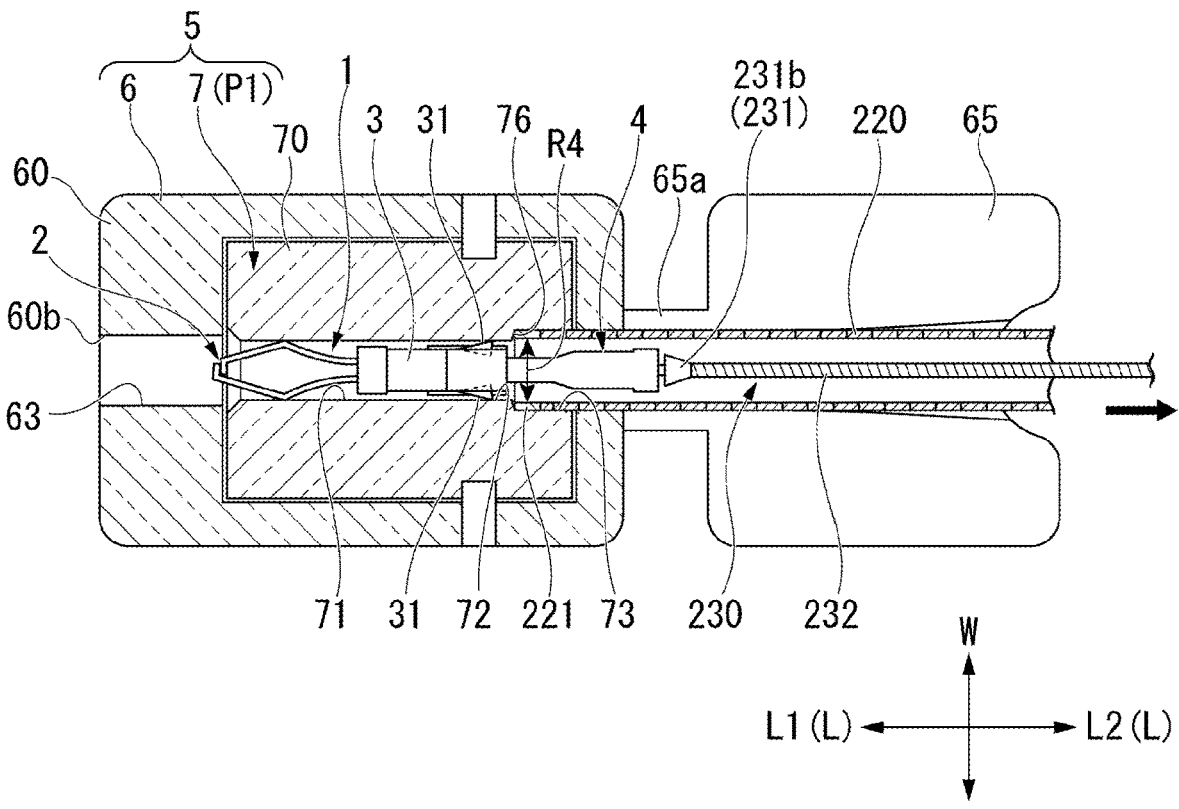
FIG. 23 is a diagram illustrating the clip unit which is loaded into a sheath of the clip introduction device.

FIG. 23 is a diagram illustrating the clip unit 1 which is loaded into the sheath 220.

A user can pull the operating wire 230. The clip 2 of the clip unit 1 can be pulled to the base side L2 by the connection member 4 connected to the arrowhead-shaped hook portion 231. In such an example, the hook 41*f* of the connection member 4 is not broken and can pull the connection portion 22 of the clip 2.

The direction D2 in which the protruding or retracting wing 31 of the presser tube 3 protrudes and retracts is perpendicular to the direction D1 in which the connection arm 44 of the connection member 4 can be opened and closed when seen or viewed in the length direction A. As illustrated in FIG. 20, the width W2 in the width direction W of the pair of recessed portion areas 75 may be smaller than the inner radius R2 of the second area 72. Accordingly, the protruding or retracting wing 31 passing through the second area 72 slides on a part in which the pair of recessed portion areas 75 are not formed and which is a part 72*a* of which a sectional surface perpendicular to the length direction A can have an arc shape with an inner radius R2. As a result, the protruding or retracting wing 31 passing through the second area 72 can be kept in the retracted state.

Figure 24:
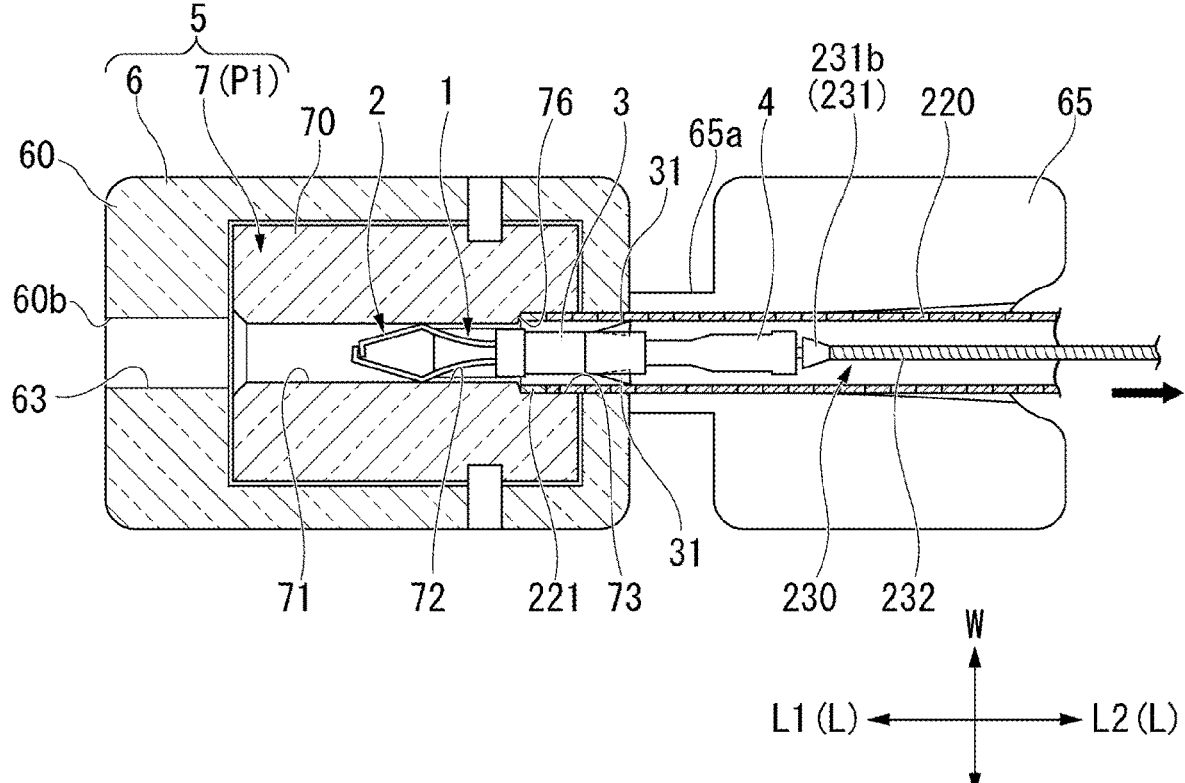
FIG. 24 is a diagram illustrating the clip unit which is loaded into the sheath.

FIG. 24 is a diagram illustrating the clip unit 1 which is loaded into the sheath 220.

A user can further pull the clip unit 1 to the base side L2. The clip unit 1 can move to the base side L2 through the first path 51 (the arm accommodation portion 63, the first area 71, and the second area 72) and can be pulled into the sheath 220.

An inner radius R4 of the sheath 220 may be larger than the inner radius R2 of the second area 72. Accordingly, the protruding or retracting wing 31 kept in the retracted state in the second area 72 can be smoothly pulled into the sheath 220. The protruding or retracting wing 31 pulled into the sheath 220 can be kept in the retracted state.

Figure 25:
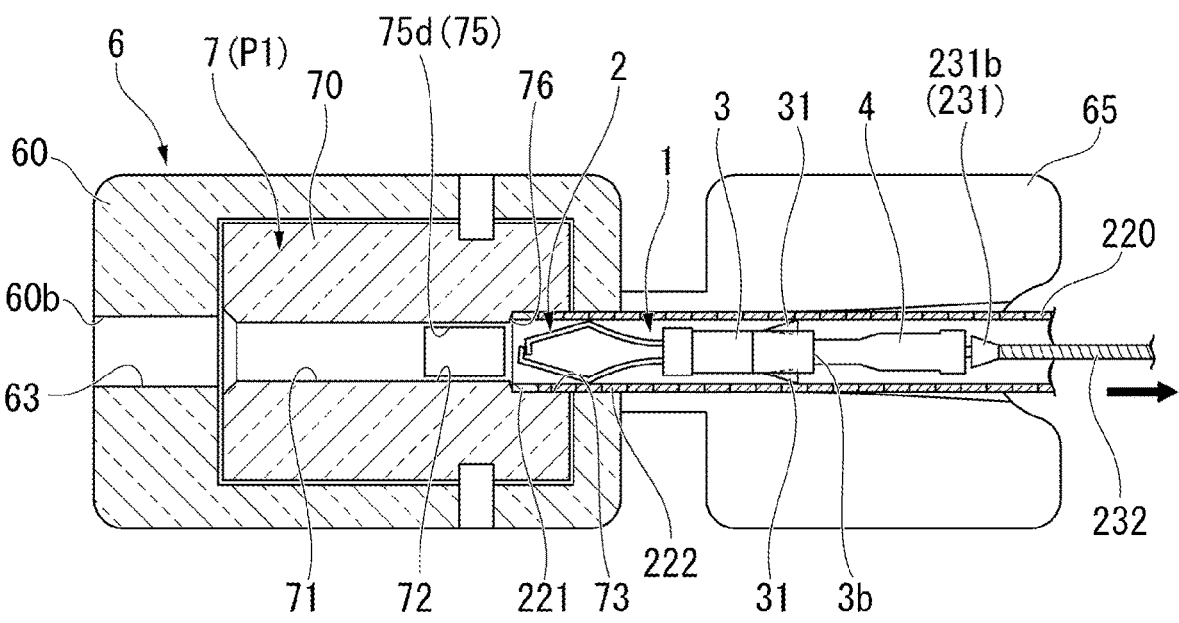
FIG. 25 is a diagram illustrating the clip unit loaded into the sheath.
Figure 25:
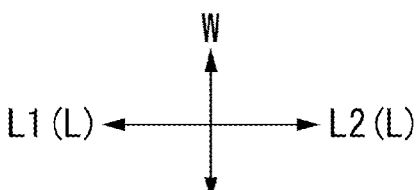

FIG. 25 is a diagram illustrating the clip unit 1 loaded into the sheath 220.

A user can further pull the clip unit 1 to the base side. The clip 2 pulled to the base side L2 can be completely pulled into the sheath 220. Accordingly, loading of the clip unit 1 into the clip introduction device 200 is completed. The user can decompress the sheath 220 with the compression portion 65 and take out or remove the sheath 220 from the first cartridge 6.

Operations and Functions of Clip Unit 1

Operations and functions of the clip unit 1 will be described below with reference to FIGS. 26 to 30.

The connection member 4 of the loaded clip unit 1 may be connected to the arrowhead-shaped hook portion 231 inserted into the sheath 220 as illustrated in FIG. 25. The protruding or retracting wing 31 can be pressed into the retracted state by the inner circumferential surface of the sheath 220.

A pair of arms 21 of the loaded clip unit 1 can be pressed into a closed state by the inner circumferential surface of the sheath 220. The engagement portion 24 can be located on the tip side of the base opening 3b, and, in the closed state, the pair of arms 21 are not or may not be locked.

Figure 26:
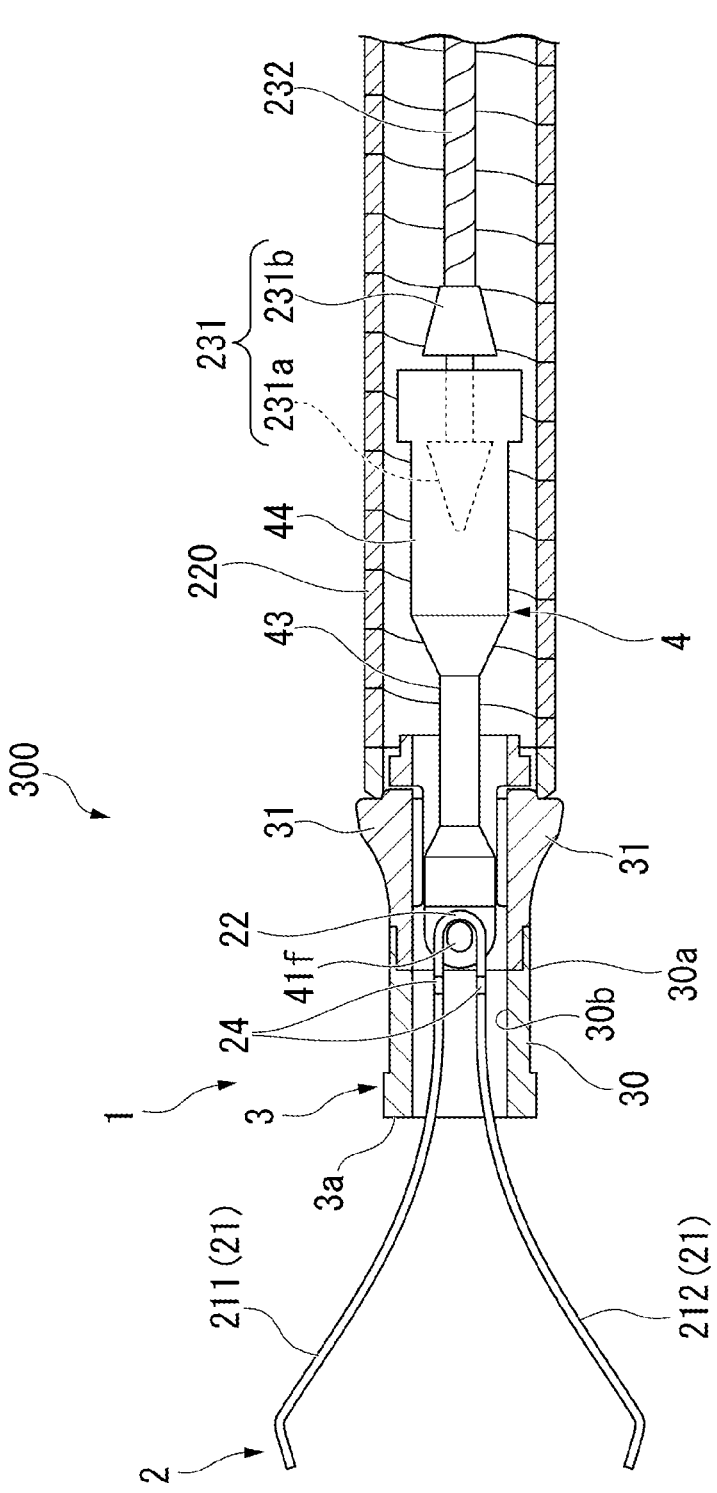
FIG. 26 is a diagram illustrating the clip unit introduced into a body.

FIG. 26 is a diagram illustrating the clip unit 1 introduced into a body.

A user can introduce the clip unit 1 loaded into the sheath 220 into a body via a channel of an endoscope. Then, the user can move the arrowhead-shaped hook portion 231 by moving the slider 242 along the operation portion body 241. The user can move the clip unit 1 until the protruding or retracting wing 31 gets out of or exits the sheath 220. When the protruding or retracting wing 31 exits the sheath 220, the protruding or retracting wing 31 can return from the retracted state to the protruded state which may be a basic posture.

When the tips of the pair of arms 21 exit the sheath 220, the clip 2 can return to the open state while moving to the tip side relative to the presser tube 3 with a self-expanding force of the pair of arms 21 as a restoring force. Even when the pair of arms 21 returns to the open state and protrudes most from the presser tube 3, the engagement portion 24 can be disposed in an internal area of the presser tube 3.

Figure 27:
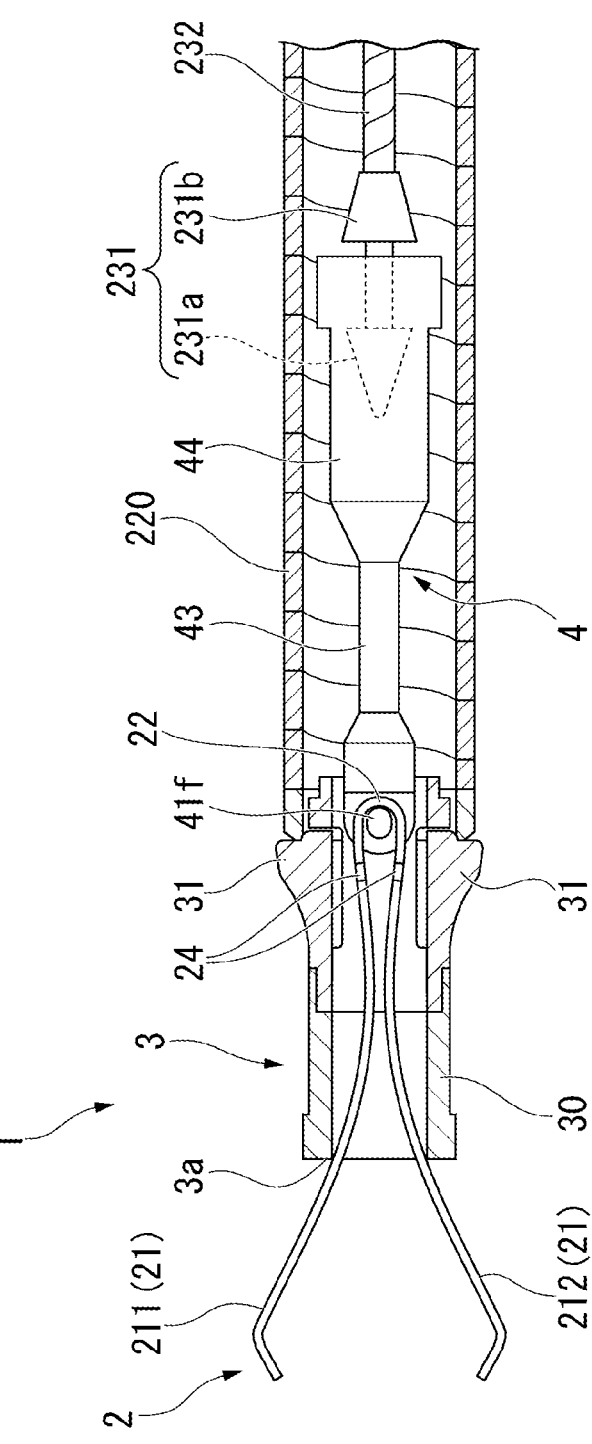
FIG. 27 is a diagram illustrating the clip unit in which a pair of arms is closed.

FIG. 27 is a diagram illustrating the clip unit 1 in which a pair of arms 21 is closed.

A user can move the arrowhead-shaped hook portion 231 backward by moving the slider 242 backward along the operation portion body 241. The connection member 4 connected to the arrowhead-shaped hook portion 231 can pull the clip 2. The pair of arms 21 with a self-expanding force can be pulled to the base side and thus presses a tip opening 3a of the presser tube to the base side. The protruding or retracting wing 31 in the protruded state can engage with the sheath 220 and thus may not be pulled into the sheath 220. Accordingly, the clip 2 pulled by the connection member 4 can be pulled into the presser tube 3.

When the connection portion 22 of the clip 2 is pulled to the base side of the presser tube 3 by the connection member 4, the pair of arms 21 can be pulled into the presser tube 3, and the pair of arms 21 can be gradually closed. When the pulling force of the connection portion 22 is released in this state, the clip 2 can return to the open state while moving to the tip side with the self-expanding force of the pair of arms 21 as a restoring force. The user can return the pair of arms 21 to the open state and re-grasp tissue.

Figure 28:
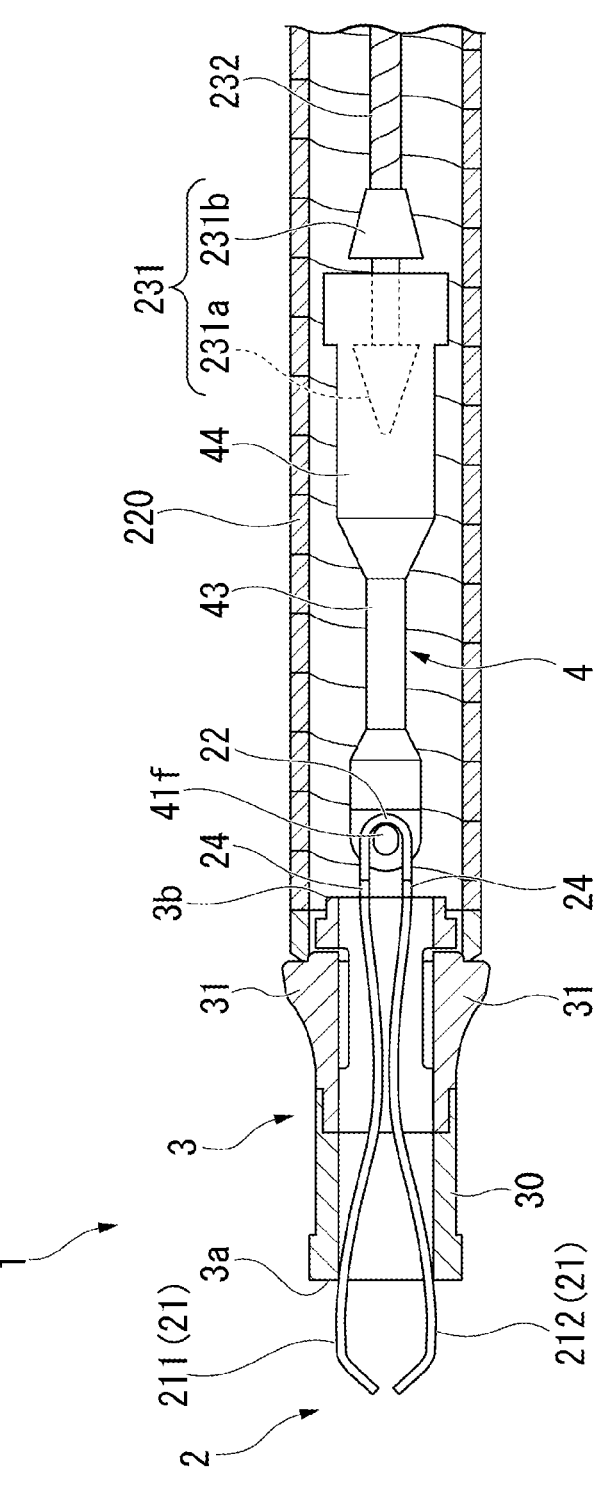
FIG. 28 is a diagram illustrating the clip unit in which clips have been locked.

FIG. 28 is a diagram illustrating the clip unit 1 of which the clip 2 has been locked.

When the connection portion 22 is further pulled to the base side of the presser tube 3, the engagement portion 24 can be pulled to the base side from the base opening 3b.

Since the connection portion 22 side of the engagement portion 24 is formed as a slope with an obtuse angle, the engagement portion 24 can be easily pulled to the base side from the base opening 3b. On the other hand, since the tissue grasping portion 23 side of the engagement portion 24 is formed as a slope with an acute angle, the engagement portion 24 and the base opening 3b can engage with each other when the engagement portion 24 is pulled to the base side from the base opening 3b. As a result, movement of the clip 2 to the tip side relative to the presser tube 3 can be regulated, and the pair of arms 21 can be locked in the closed state. When the pair of arms 21 is locked in the closed state, the pair of arms 21 cannot return to the open state.

Figure 29:
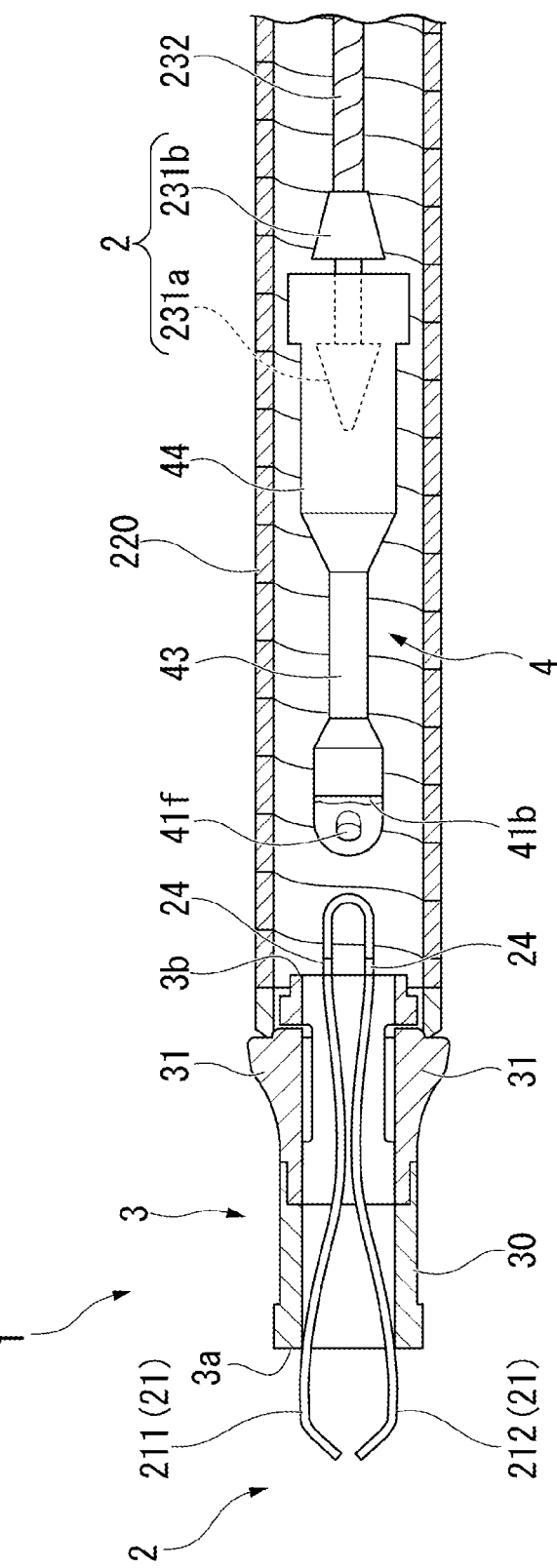
FIG. 29 is a diagram illustrating the clip unit from which the clips have been detached.

FIG. 29 is a diagram illustrating the clip unit 1 from which the clip 2 has been detached.

A user can further pull the clip 2. When a breaking force based on a pulling of 20 N to 90 N is applied to the hook 41f, the breakable portion 41b can be broken. The breaking strength of the breakable portion 41b may be made lower than the breaking strength of the connection portion body 43. Accordingly, the breakable portion 41b instead of the connection portion body 43 can be broken.

Figure 30:
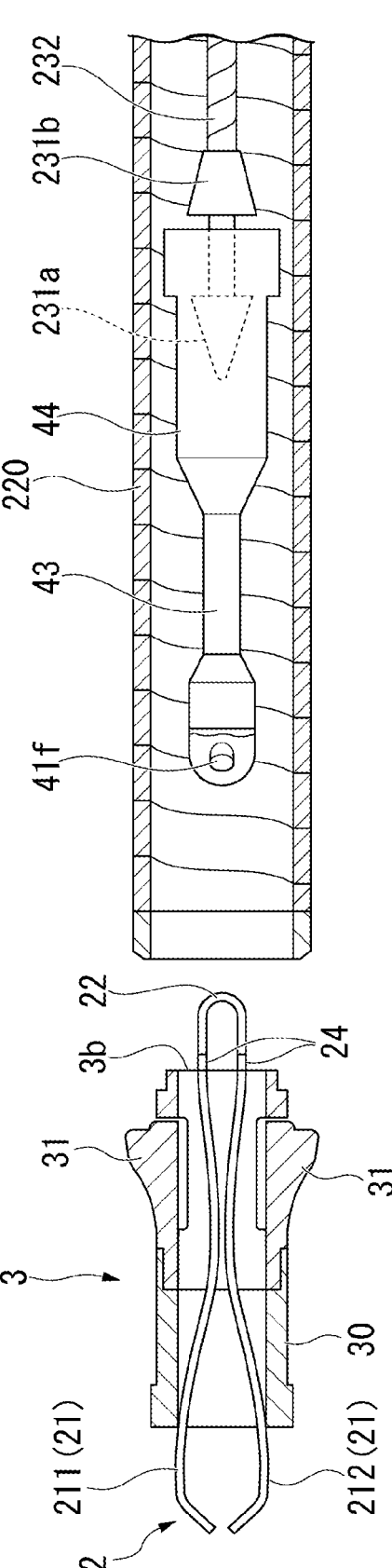
FIG. 30 is a diagram illustrating the clip unit after breakage.

FIG. 30 is a diagram illustrating the clip unit 1 after breaking has occurred.

The user can move the sheath 220 backward and leave the clip 2 having ligated tissue in the body.

The user can re-store a new clip unit 1 into the cartridge 5 which is empty after the clip unit 1 has been used and can reload the new clip unit 1 into the applicator.

With the cartridge system 100 according to this embodiment, the cartridge 5 can re-store a clip unit 1 and repeatedly reload a clip unit 1 into the clip introduction device 200. After a clip unit 1 has been reloaded into the clip introduction device 200 from the cartridge 5, the cartridge 5 is not discarded and can be reused.

While the first embodiment of the present disclosure has been described above in details with reference to the drawings, a specific configuration is not limited to this embodiment and includes a change in design without departing from scope of the present disclosure. Elements described in the aforementioned embodiment and following modified examples can be appropriately combined into a configuration.

Modified Example 1

Figure 31:
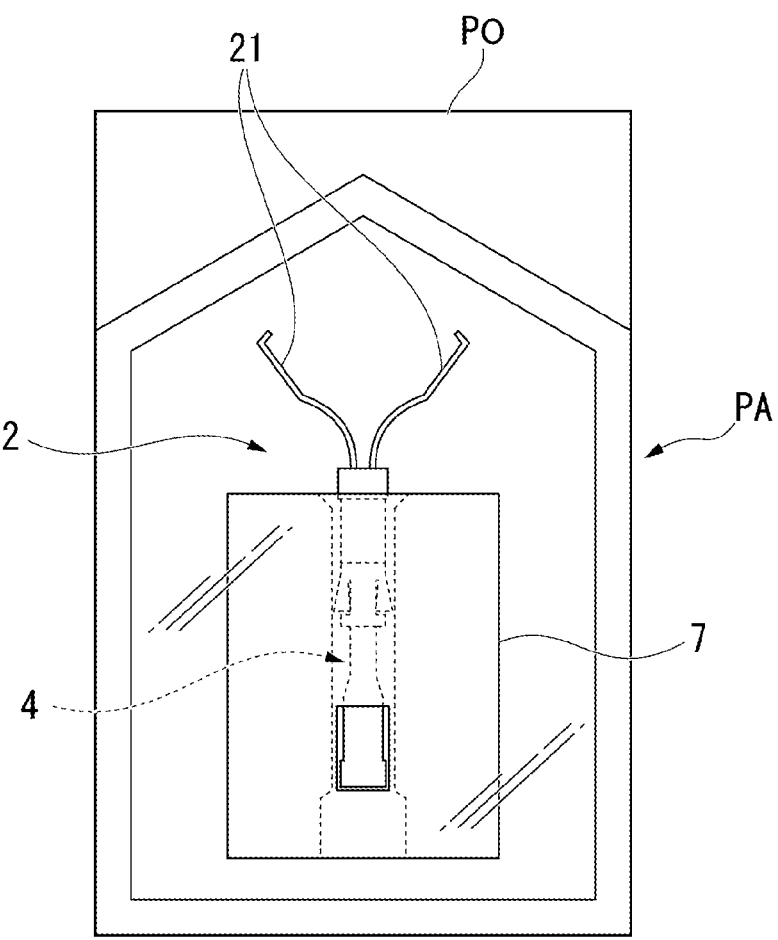
FIG. 31 is a diagram illustrating another mode of a clip unit enclosed in a sterilized pack.

In an example, the clip unit 1 is enclosed in a sterilized pack PA, and the clip unit 1 can be stored in the second cartridge 7 after the sterilized pack PA has been unsealed. However, a mode in which the clip unit 1 is enclosed in the sterilized pack PA is not limited thereto. FIG. 31 is a diagram illustrating another mode of the clip unit 1 which is enclosed in a sterilized pack PA. The clip unit 1 may be enclosed in a sterilized pack PA in a mode in which the clip unit 1 is stored in advance in the second cartridge 7.

In this case, the second cartridge 7 can be attached to and detached from the first cartridge 6. A user can accommodate or store the second cartridge 7 in which the clip unit 1 is stored in advance in the first cartridge 6 and dispose the second cartridge 7 at the first position P1.

Second Embodiment

A second embodiment of the present disclosure will be described below with reference to FIGS. 32 to 35. In the following description, the same elements as described above will be referred to by the same reference signs, and repeated description thereof will be omitted.

Figure 32:
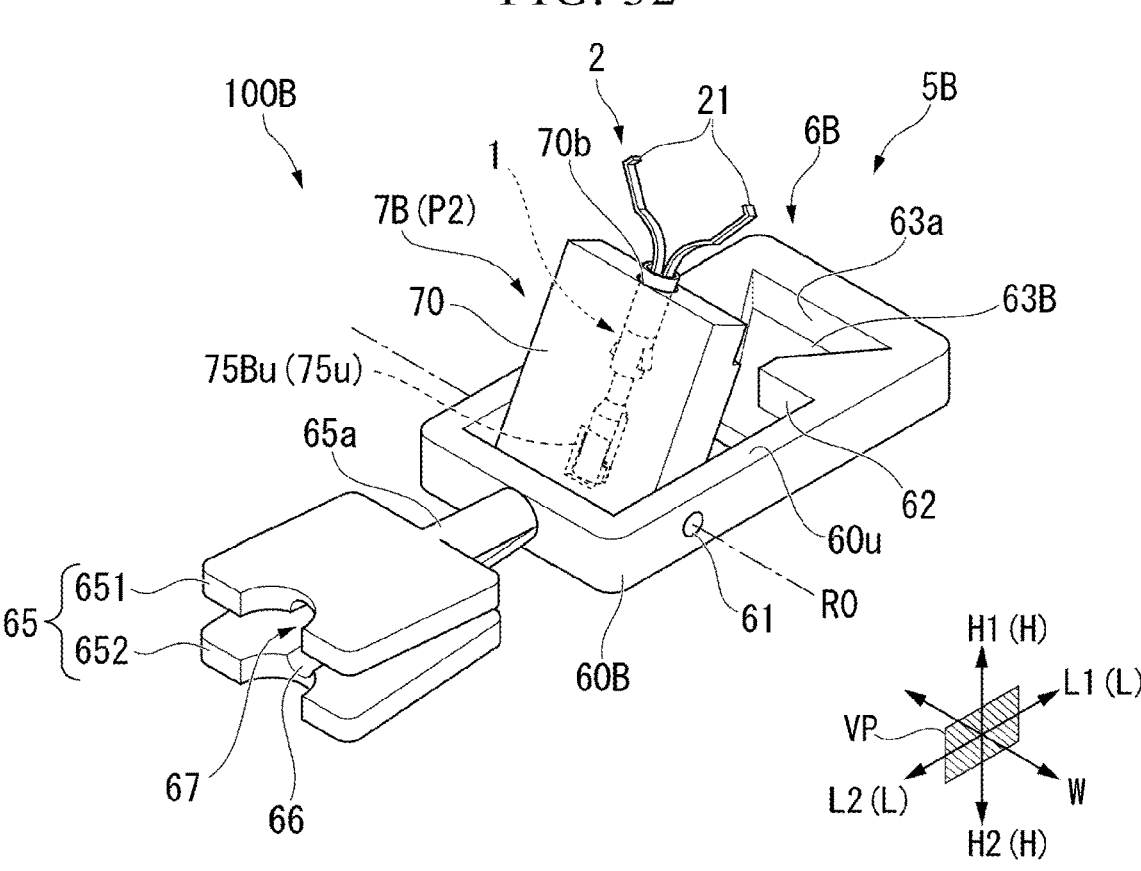
FIG. 32 is a perspective view of a cartridge system according to a second embodiment.
Figure 33:
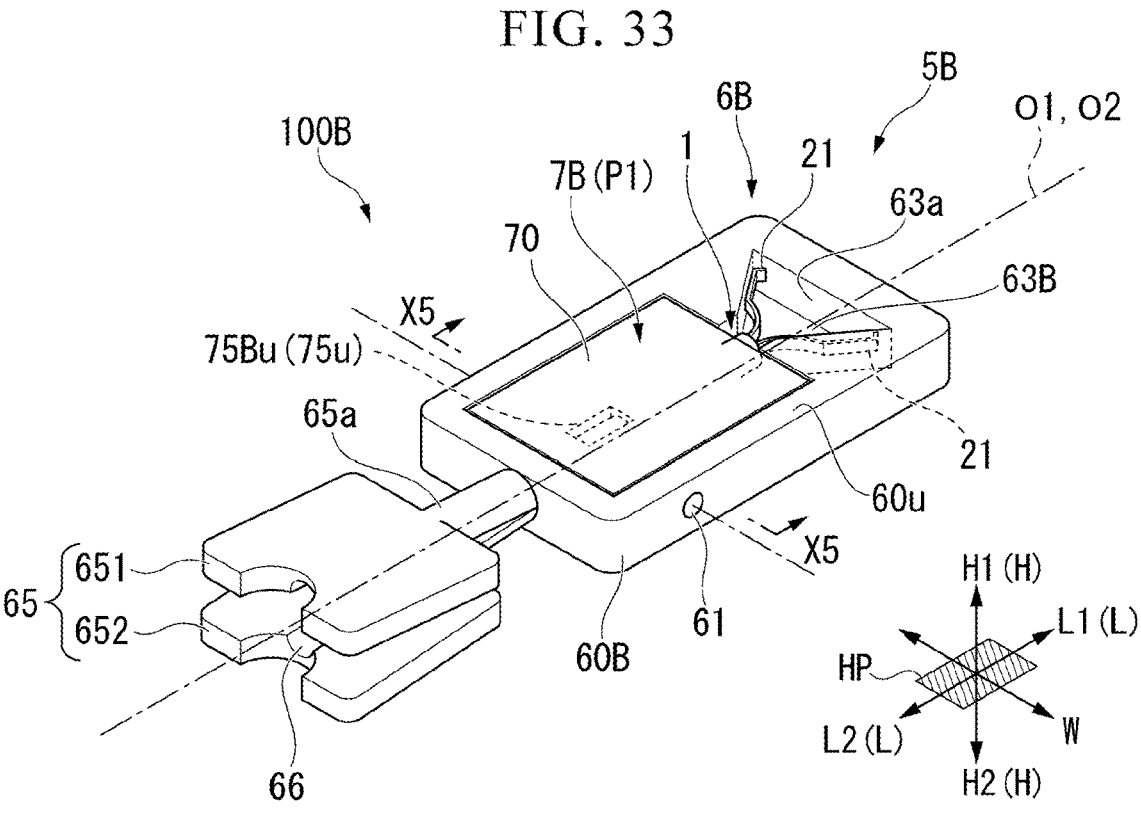
FIG. 33 is a perspective view of the cartridge system.

FIGS. 32 and 33 are perspective views of a cartridge system 100B.

A cartridge system 100B according to this embodiment may include a clip unit 1 and a cartridge 5B that accommodates the clip unit 1. The cartridge system 100B may be a support system that can allow the clip unit 1 to be easily loaded into a clip introduction device 200.

Figure 34:
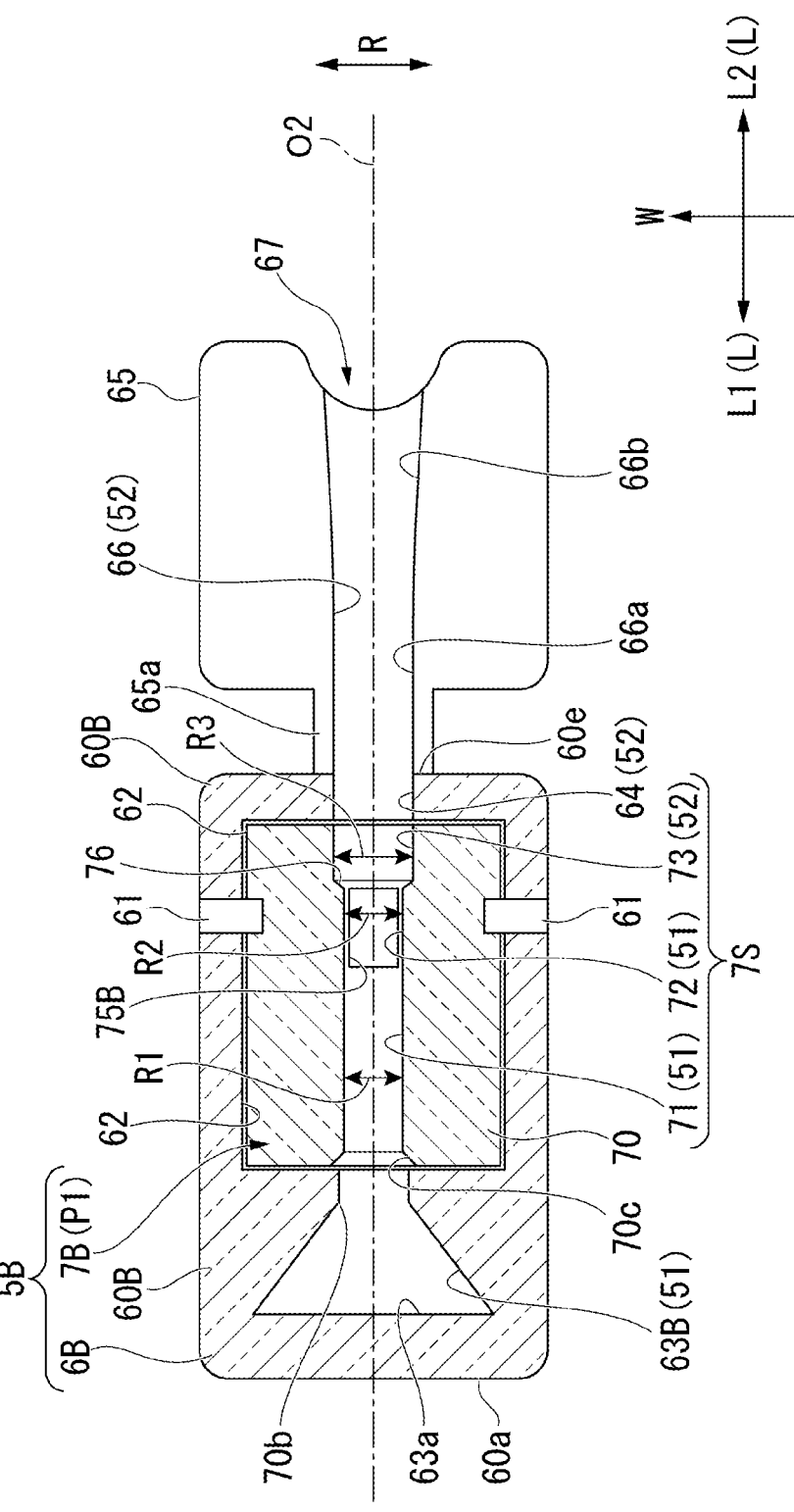
FIG. 34 is a sectional view of a cartridge of the cartridge system.

FIG. 34 is a sectional view of the cartridge 5B.

The cartridge 5B may be a case in which the clip unit 1 is stored similarly to the cartridge 5 according to the first embodiment. The cartridge 5B may include a first cartridge 6B and a second cartridge 7B. The second cartridge 7B can be accommodated or stored in the first cartridge 6B as illustrated in FIG. 33. The second cartridge 7B can be rotatably attached to the first cartridge 6B as illustrated in FIG. 32.

The first cartridge 6B may include a cartridge outer circumferential portion 60B, a compression portion 65, and a sheath connection portion 66.

The cartridge outer circumferential portion 60B may be formed in a substantially rectangular box shape. A length in the width direction W of the cartridge outer circumferential portion 60B may be larger than a length in the height direction H of the cartridge outer circumferential portion 60B. The cartridge outer circumferential portion 60B may include a second cartridge support portion 61, a second cartridge accommodation portion 62, and an arm accommodation portion 63B.

The arm accommodation portion 63B may be a recessed portion that is formed in the top surface 60u of the cartridge outer circumferential portion 60B and may be open to the top side H1 in the height direction H. The arm accommodation portion 63B may not communicate with, touch, contact, or the like a tip 60a of the cartridge outer circumferential portion 60B on the tip side L1. The arm accommodation portion 63B may communicates with, contact, touch, or the like the second cartridge accommodation portion 62 on the base side L2. The length in the width direction W of the arm accommodation portion 63B may be enlarged from the tip side L1 to the base side L2, and tips of a pair of arms 21 in an open state can be accommodated or stored therein.

Figure 35:
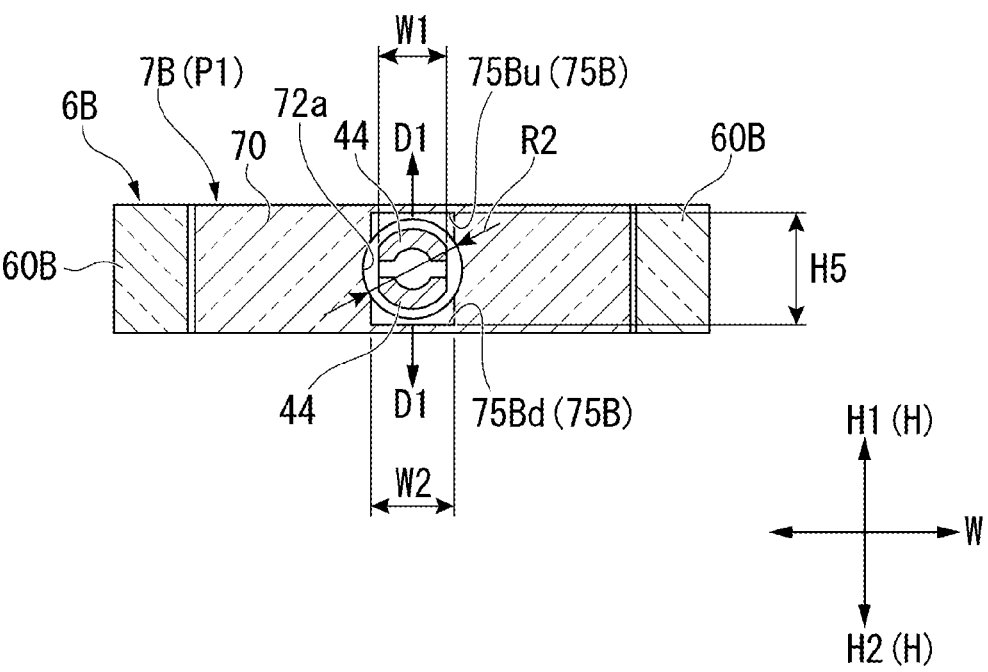
FIG. 35 is a sectional view of a second area taken along line X5-X5 in FIG. 33.

FIG. 35 is a sectional view of the second area 72 taken along line X5-X5 in FIG. 33.

The second cartridge 7B may be the same as the second cartridge 7 according to the first embodiment except for a pair of recessed portion areas 75. In the second area 72 of the second cartridge 7B, a pair of recessed portion areas 75B (an upper recessed portion area 75Bu and a lower recessed portion area 75Bd) that are recessed outward in the radial direction R may be formed on the top side H1 and the bottom side H2 in the height direction H. In this embodiment, the pair of recessed portion areas 75B (the upper recessed portion area 75Bu and the lower recessed portion area 75Bd) do not penetrate the cartridge body 70.

A length H5 in the height direction H of a hollow area of the second area 72 in which the pair of recessed portion areas 75B are formed may be much larger than the inner radius R2. The length H5 may be larger than a maximum length H4 (see FIG. 21) in the height direction H of the connection arm 44 in the open state. Accordingly, the connection arm 44 disposed in the second area 72 in which the pair of recessed portion areas 75B are formed can be opened (elastically enlarged) in the height direction H until the arrowhead-shaped hook portion 231 can be inserted to the gap in the connection arm 44 similarly to the first embodiment.

When the second cartridge 7B is located at the first position P1, the arm accommodation portion 63B of the first cartridge 6B and the first area 71 and the second area 72 of the cartridge body 70 of the second cartridge 7B can form a first path 51 (also referred to as a clip unit path 51 of the cartridge 5B) extending in the length direction L.

When the second cartridge 7B is located at the first position P1, the sheath connection portion 66 and the sheath insertion portion 64 of the first cartridge 6B and the sheath insertion area 73 of the cartridge body 70 of the second cartridge 7B can form a second path 52 (also referred to as a sheath path 52 of the cartridge 5B) extending in the length direction L.

The first path 51 and the second path 52 can form a continuous space extending in the length direction L of the cartridge 5B.

In the clip unit 1 stored in the cartridge 5 as illustrated in FIG. 33, the connection arm 44 of the connection member 4 may be disposed in the second area 72. Accordingly, a user does not need to position the clip unit 1 such that the connection arm 44 of the connection member 4 of the clip unit 1 can be disposed in the second area 72 similarly to the first embodiment.

When the clip unit 1 is loaded into the clip introduction device 200 using the cartridge 5B, the pair of arms 21 can come into contact with a wall 63a of the tip side L1 of the arm accommodation portion 63B and thus the clip unit 1 does not move in the length direction (moving direction) L. Accordingly, a user can easily load the clip unit 1 into the clip introduction device 200.

With the cartridge system 100B according to this embodiment, the cartridge 5B can re-store a clip unit 1 and repeatedly reload a clip unit 1 into the clip introduction device 200. After a clip unit 1 has been reloaded into the clip introduction device 200 from the cartridge 5B, the cartridge 5B may not be discarded and may be reused.

While the second embodiment of the present disclosure has been described above in details with reference to the drawings, a specific configuration is not limited to this embodiment and includes a change in design without departing from the scope of the present disclosure. Elements described in the aforementioned embodiment and following modified examples can be appropriately combined into a configuration.

Modified Example 2

Similar to Modified Example 1 above, the clip unit 1 may be enclosed in a sterilized pack PA in a mode in which the clip unit 1 is stored in the second cartridge 7B in advance. In this case, the second cartridge 7B can be attached to and detached from the first cartridge 6B. A user can accommodate or store the second cartridge 7B in which the clip unit 1 is stored in advance in the first cartridge 6B and dispose the second cartridge 7B at the first position P1.

Third Embodiment

A third embodiment of the present disclosure will be described below with reference to FIGS. 36 to 38. In the following description, the same elements as described above will be referred to by the same reference signs, and repeated description thereof will be omitted.

Figure 36:
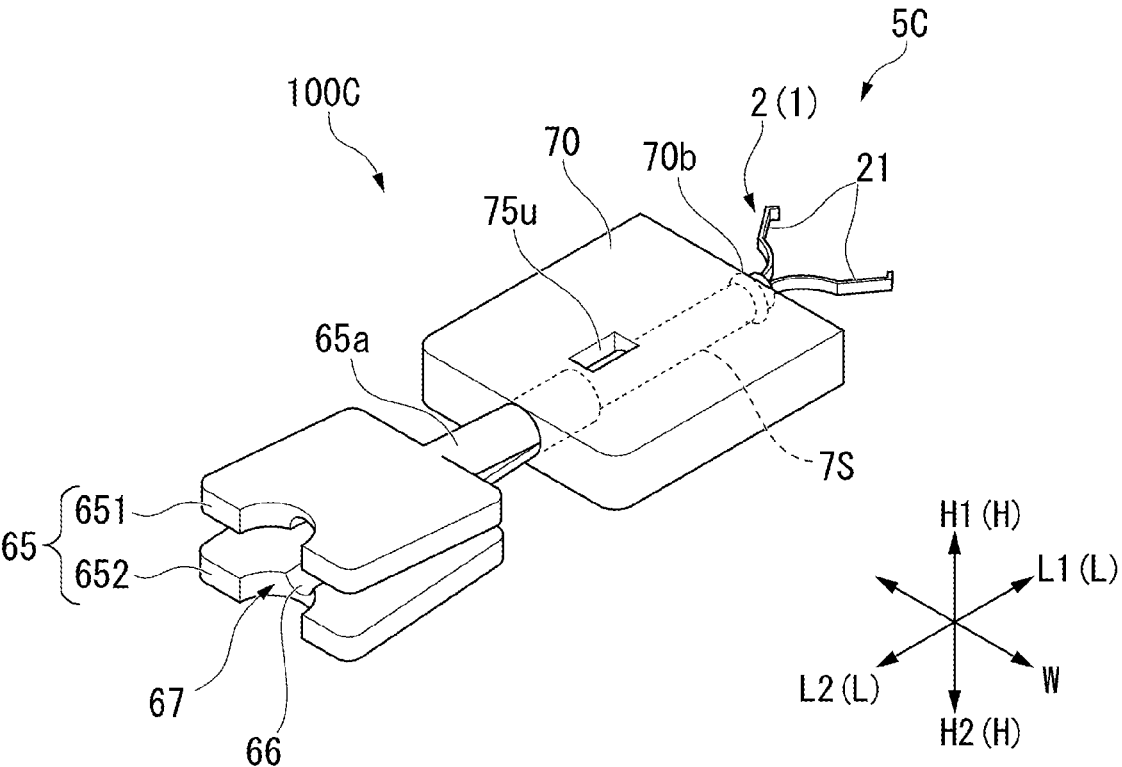
FIG. 36 is a perspective view of a cartridge system according to a third embodiment.

FIG. 36 is a perspective view of a cartridge system 100C.

A cartridge system 100C according to this embodiment may include a clip unit 1 and a cartridge 5C that accommodates the clip unit 1. The cartridge system 100C may be a support system that allows the clip unit 1 to be easily loaded into a clip introduction device 200. In an example, clip unit 1 may not accommodated or stored in the cartridge 5C in advance. When the clip unit 1 is loaded into the clip introduction device 200, a user can accommodate or store the clip unit 1 in the cartridge 5C as illustrated in FIG. 36.

Figure 37:
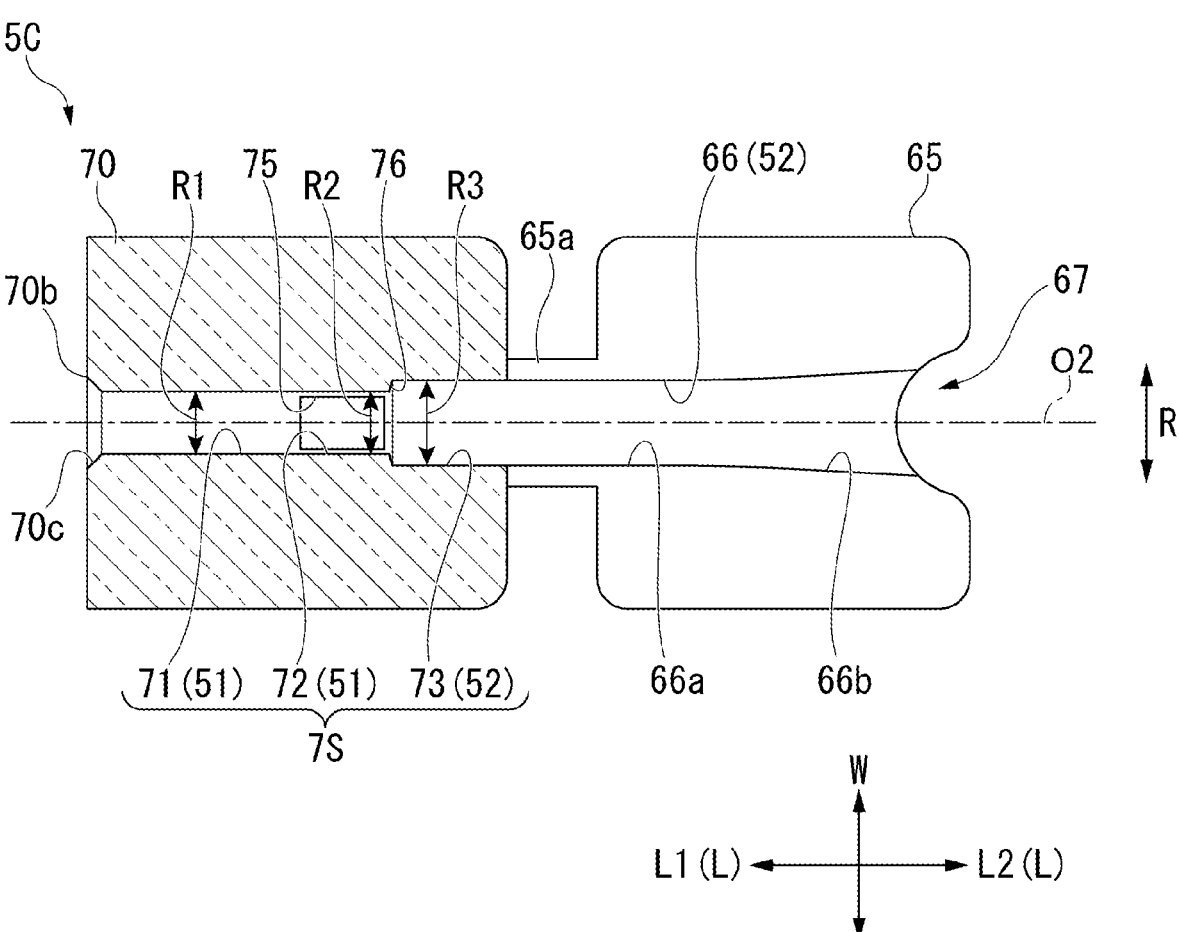
FIG. 37 is a sectional view of a cartridge of the cartridge system.

FIG. 37 is a sectional view of the cartridge 5C.

The cartridge 5C may be a case in which the clip unit 1 is stored similarly to the cartridge 5 according to the first embodiment. The cartridge 5C may be an integrated cartridge (also referred to as a main cartridge) in which a first path 51 and a second path 52 can be formed. In this example, the cartridge 5C is not partitioned into two cartridges unlike the cartridge 5 according to the first embodiment and the cartridge 5B according to the second embodiment.

The cartridge 5C may include a cartridge body 70, a compression portion 65, and a sheath connection portion 66. The connection portion 65a of the compression portion 65 can be connected to the cartridge body 70. The sheath insertion area 73 of the cartridge body 70 can communicates with, connect, contact, touch, or the like the sheath connection portion 66.

The first area 71 and the second area 72 of the cartridge body 70 can form the first path 51 (also referred to as a clip unit path 51 of the cartridge 5C) extending in the length direction L.

The sheath connection portion 66 and the sheath insertion area 73 of the cartridge body 70 can form the second path 52 (also referred to as a sheath path 52 of the cartridge 5C) extending in the length direction L.

The first path 51 and the second path 52 can form a continuous space extending in the length direction L of the cartridge 5C.

Figure 38:
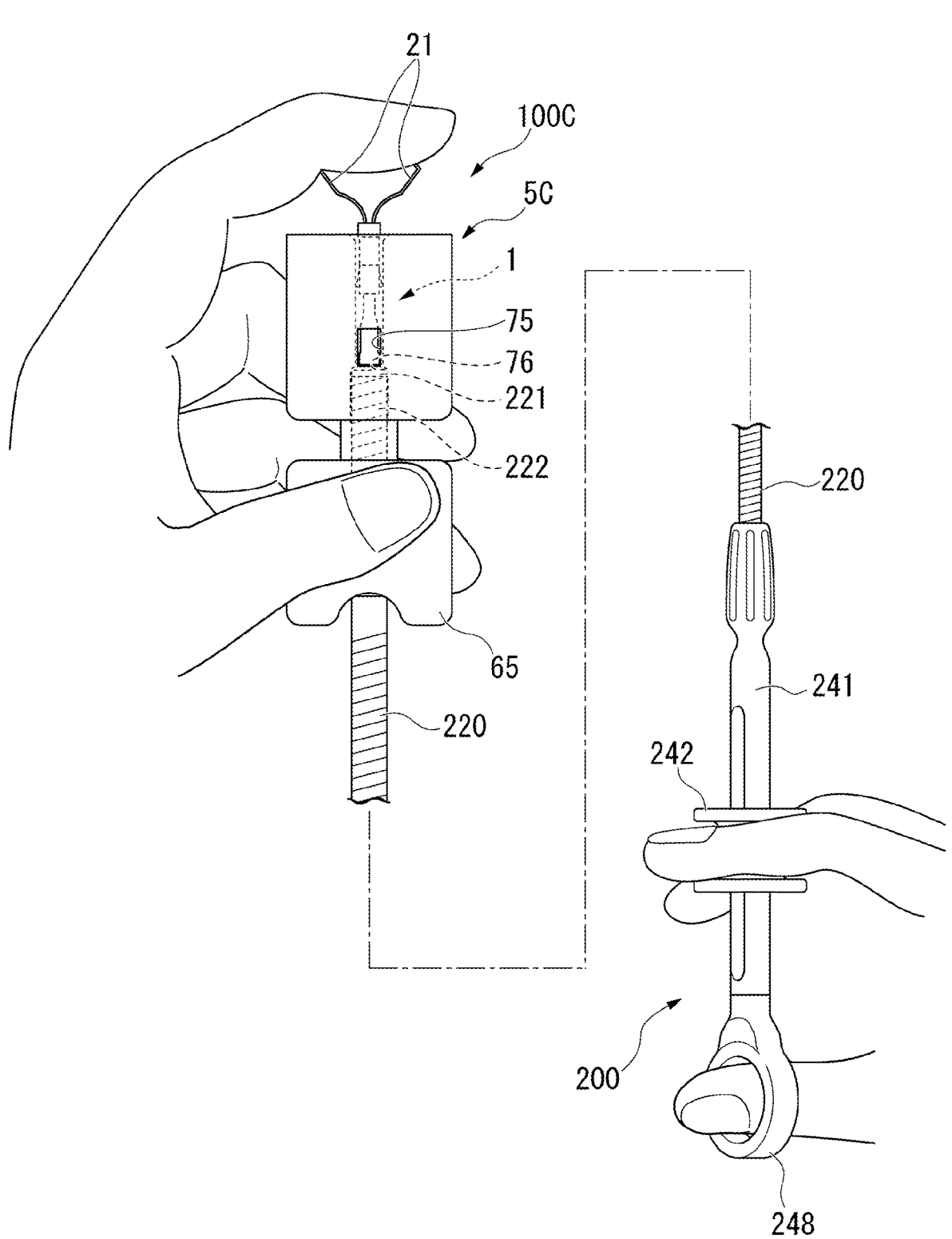
FIG. 38 is a diagram illustrating an operation of loading a clip unit.

FIG. 38 is a diagram illustrating an operation of loading the clip unit 1.

A user can insert the clip unit 1 into the clip unit insertion port 70b and store the clip unit 1 in the storage area 7S of the cartridge 5C. The user can insert the sheath 220 into the second path 52 (the sheath connection portion 66 and the sheath insertion area 73) via the insertion port 67 and bring the distal tip 221 of the sheath 220 into contact with the sheath contact portion 76 of the sheath insertion area 73. The user can fix the sheath 220 to the cartridge 5C by compressing the sheath 220 with the compression portion 65. The user can fix a pair of arms 21 with fingers such that the pair of arms 21 do not move to the tip side L1.

The user can connect the arrowhead-shaped hook portion 231 to the connection member 4 by moving the slider 242 relative to the operation portion body 241 of the operation portion 240 and moving the operating wire 230 relative to the sheath 220.

With the cartridge system 100C according to this embodiment, the cartridge 5C can re-store a clip unit 1 and repeatedly reload a clip unit 1 into the clip introduction device 200. After a clip unit 1 has been reloaded into the clip introduction device 200 from the cartridge 5C, the cartridge 5C may not discarded and may be reused. For example, the cartridge 5C may be sold separately from the clip unit 1. By allowing a user to separately purchase the cartridge 5C, it is possible to enhance efficiency of the operation of reloading the clip unit 1 into the clip introduction device 200.

While the third embodiment of the present disclosure has been described above in details with reference to the drawings, a specific configuration is not limited to this embodiment and includes a change in design without departing from the scope of the present disclosure. Elements described in the aforementioned embodiment and following modified examples can be appropriately combined into a configuration.

Fourth Embodiment

A fourth embodiment of the present disclosure will be described below with reference to FIGS. 39 to 44. In the following description, the same elements as described above will be referred to by the same reference signs, and repeated description thereof will be omitted.

Figure 39:
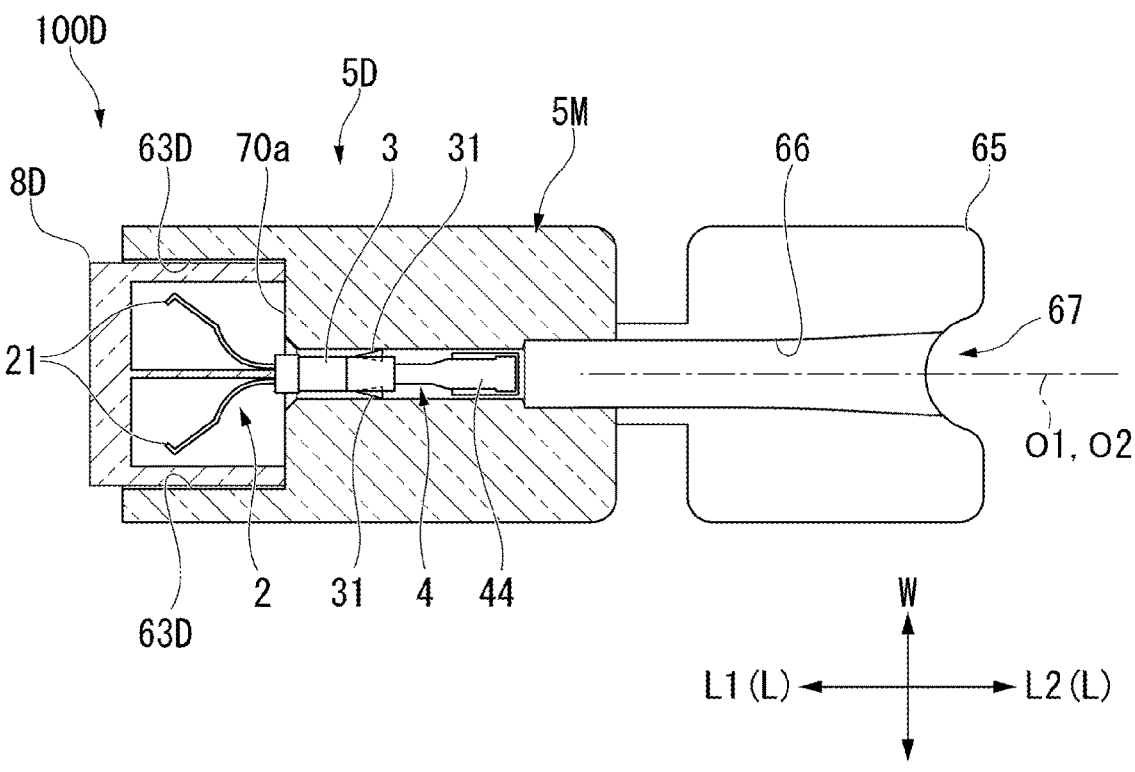
FIG. 39 is a diagram illustrating a cartridge system according to a fourth embodiment.

FIG. 39 is a diagram illustrating a cartridge system 100D.

A cartridge system 100D according to this embodiment may include a clip unit 1, a cartridge 5D that can accommodate or store the clip unit 1, and an auxiliary cartridge 8D. The cartridge system 100D may be a support system that allows the clip unit 1 to be easily loaded into a clip introduction device 200.

Figure 40:
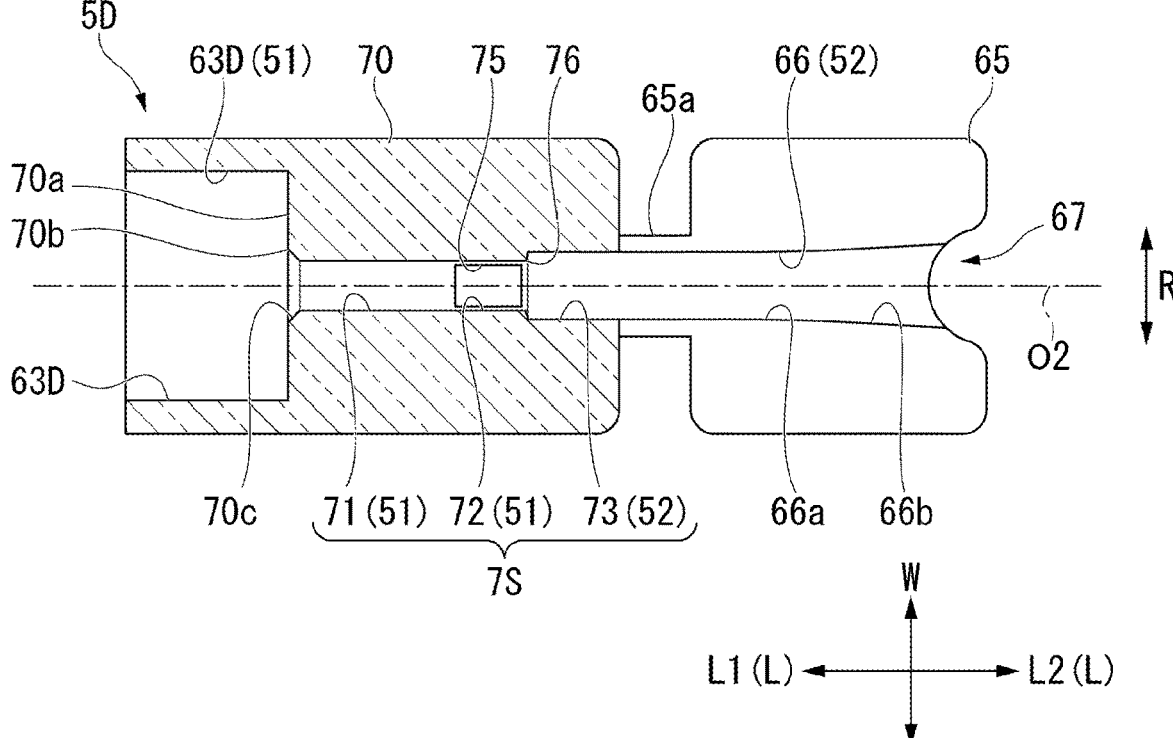
FIG. 40 is a sectional view of a cartridge of the cartridge system.

FIG. 40 is a sectional view of the cartridge 5D.

The cartridge 5D may be a case in which the clip unit 1 can be stored similarly to the cartridge 5 according to the first embodiment. Similar to the cartridge 5C according to the third embodiment, the cartridge 5D may be an integrated cartridge (also referred to as a main cartridge) in which a first path 51 and a second path 52 can be formed.

The cartridge 5D may include an arm accommodation portion 63D, a cartridge body 70, a compression portion 65, and a sheath connection portion 66. The connection portion 65a of the compression portion 65 may be connected to the cartridge body 70. The sheath insertion area 73 of the cartridge body 70 can communicate with, touch, connect with, contact, or the like the sheath connection portion 66.

The arm accommodation portion 63D may be provided on the tip side L1 of the tip 70a of the cartridge body 70 and is formed on both sides with the center axis O2 of the cartridge 5D interposed therebetween. The arm accommodation portion 63D can accommodate the tips of a pair of arms 21 in the open state. As illustrated in FIG. 39, the auxiliary cartridge 8D can be attached to the arm accommodation portion 63D.

Figure 41:
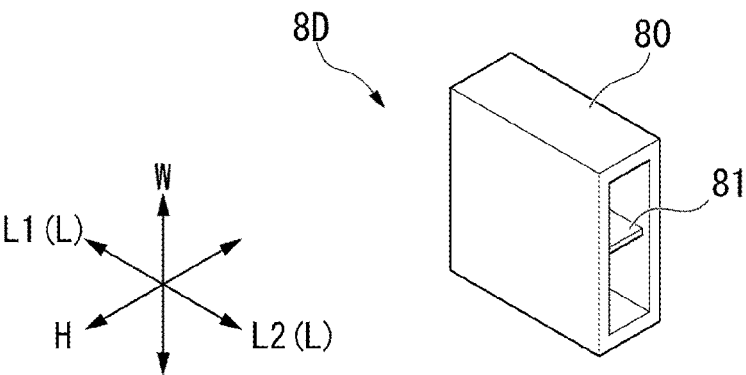
FIG. 41 is a perspective view of an auxiliary cartridge of the cartridge system.

FIG. 41 is a perspective view of the auxiliary cartridge 8D.

The auxiliary cartridge 8D may be a cartridge that can be attached to the arm accommodation portion 63D and assists with storing of the clip unit 1 in the cartridge 5D. The auxiliary cartridge 8D includes an auxiliary cartridge body 80 with a bottomed angular tube shape and a central protrusion 81 that can be provided in the internal space of the auxiliary cartridge body 80 and extends in the length direction L.

Figure 42:
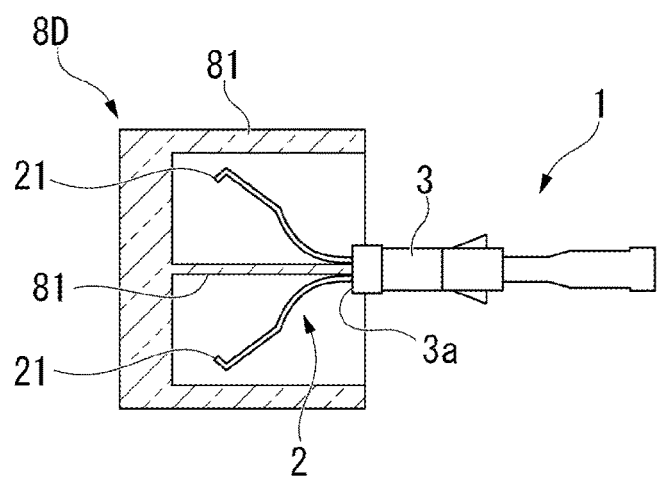
FIG. 42 is a diagram illustrating a method of storing a clip unit in the cartridge.
Figure 43:
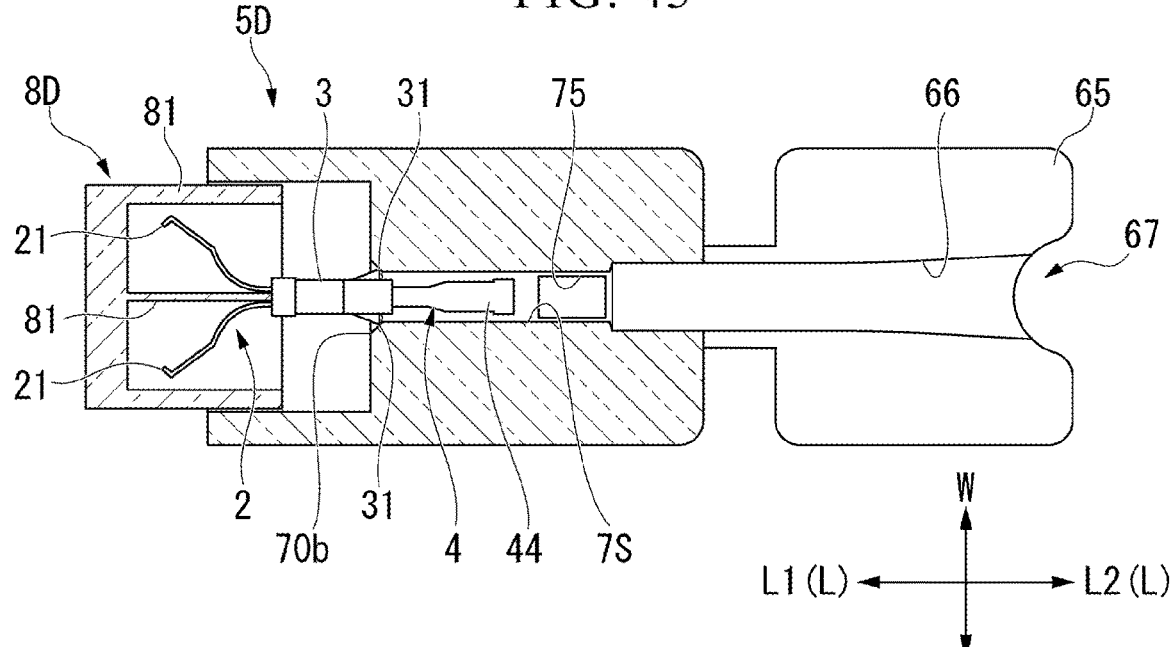
FIG. 43 is a diagram illustrating a method of storing the clip unit in the cartridge.

FIGS. 42 and 43 are diagrams illustrating a method of storing the clip unit 1 in the cartridge 5D using the auxiliary cartridge 8D. A user can accommodate or store tips of a pair of arms 21 of the clip unit 1 in the auxiliary cartridge body 80 as illustrated in FIG. 42. The user can bring the tip opening 3a of the presser tube 3 into contact with the central protrusion 81. Then, the user can insert the clip unit 1 into the clip unit insertion port 70b and stores the clip unit 1 in the storage area 7S of the cartridge 5D by accommodating or storing the auxiliary cartridge 8D in the arm accommodation portion 63 as illustrated in FIG. 43.

In the clip unit 1 stored in the cartridge 5D as illustrated in FIG. 39, the connection arm 44 of the connection member 4 can be disposed in the second area 72.

Accordingly, a user does not need to position the clip unit 1 such that the connection arm 44 of the connection member 4 of the clip unit 1 can be disposed in the second area 72 similarly to the first embodiment.

Figure 44:
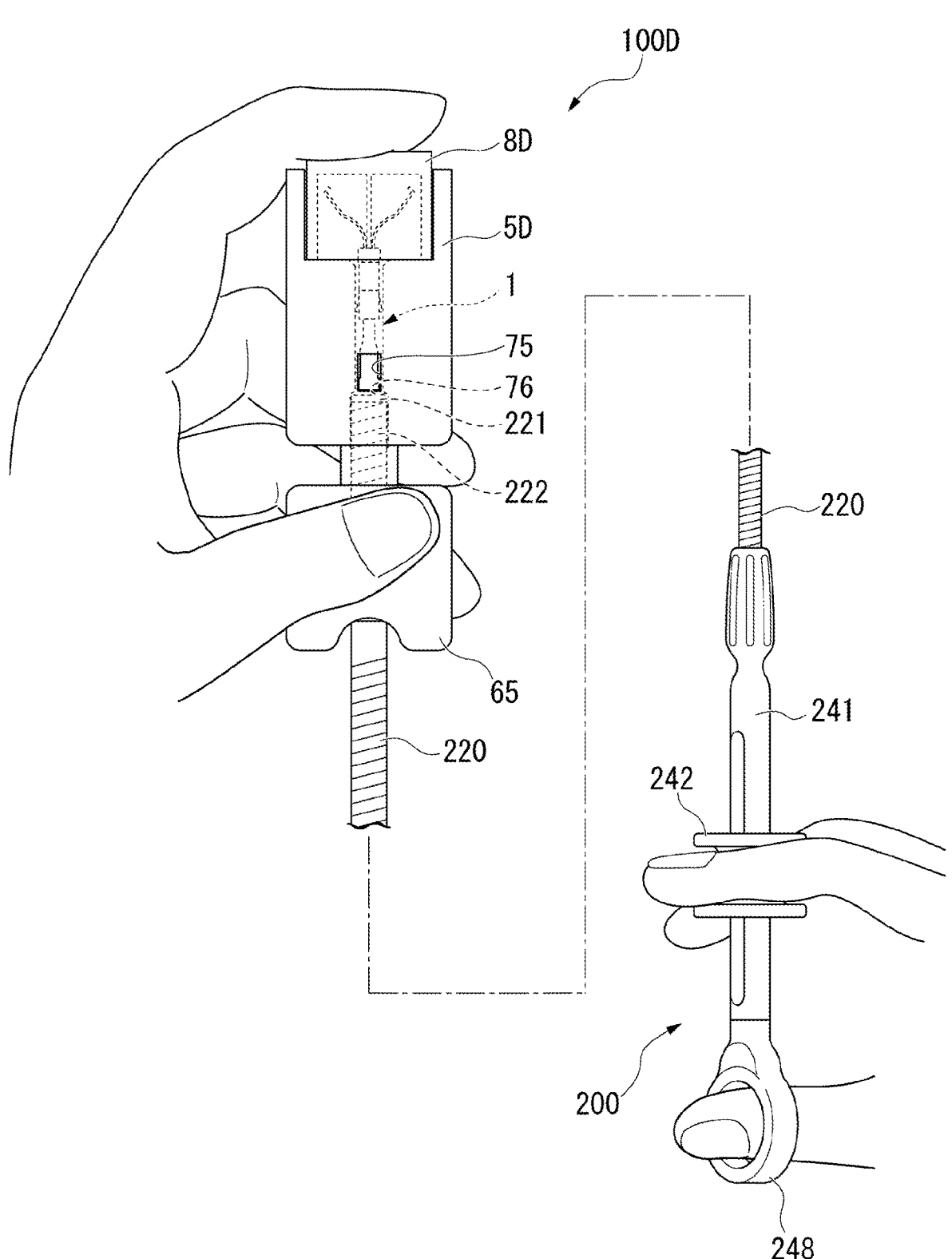
FIG. 44 is a diagram illustrating an operation of loading the clip unit.

FIG. 44 is a diagram illustrating an operation of loading the clip unit 1.

A user can insert the sheath 220 into the second path 52 (the sheath connection portion 66 and the sheath insertion area 73) via the insertion port 67 and bring the distal tip 221 of the sheath 220 into contact with the sheath contact portion 76 of the sheath insertion area 73. The user can fix the sheath 220 to the cartridge 5D by compressing the sheath 220 with the compression portion 65. The user can fix the auxiliary cartridge 8D with fingers such that the pair of arms 21 do not move to the tip side L1.

The user can connect the arrowhead-shaped hook portion 231 to the connection member 4 by moving the slider 242 forward relative to the operation portion body 241 of the operation portion 240 and moving the operating wire 230 forward relative to the sheath 220.

When the clip unit 1 may be loaded into the clip introduction device 200 using the cartridge 5D, the tip opening 3a of the presser tube 3 can comes into contact with the central protrusion 81 of the auxiliary cartridge 8D and thus the clip unit 1 may not move forward in the length direction (moving direction) L. Accordingly, a user can easily load the clip unit 1 into the clip introduction device 200.

With the cartridge system 100D according to this embodiment, the cartridge 5D can re-store a clip unit 1 and repeatedly reload a clip unit 1 into the clip introduction device 200. After a clip unit 1 has been reloaded into the clip introduction device 200 from the cartridge 5D, the cartridge 5D may not discarded and may be reused.

While the fourth embodiment of the present disclosure has been described above in details with reference to the drawings, a specific configuration is not limited to this embodiment and includes a change in design without departing from the scope of the present disclosure. Elements described in the aforementioned embodiment and following modified examples can be appropriately combined into a configuration.

Modified Example 3

Figure 45:
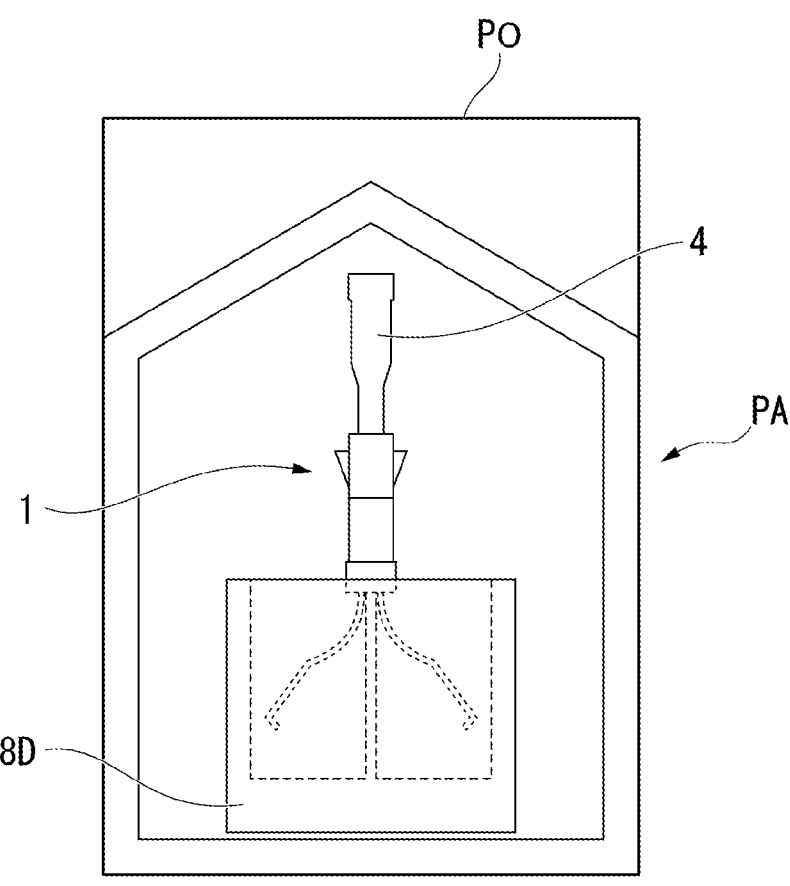
FIG. 45 is a diagram illustrating a mode of the clip unit enclosed in a sterilized pack.

FIG. 45 is a diagram illustrating a mode of a clip unit 1 enclosed in a sterilized pack PA. A clip unit 1 may be enclosed in a sterilized pack PA in a state in which it is stored in advance in the auxiliary cartridge 8D. The clip unit 1 may be enclosed in the sterilized pack PA such that the connection member 4 of the clip unit 1 can face an unsealing opening PO of the sterilized pack PA.

Figure 48:
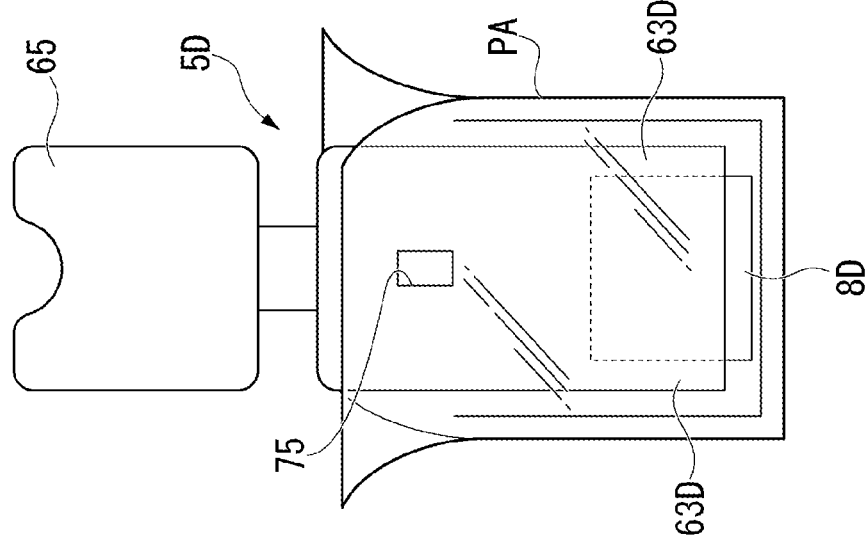
FIG. 48 is a diagram illustrating a method of storing the clip unit enclosed in the sterilized pack in the cartridge.
Figure 47:
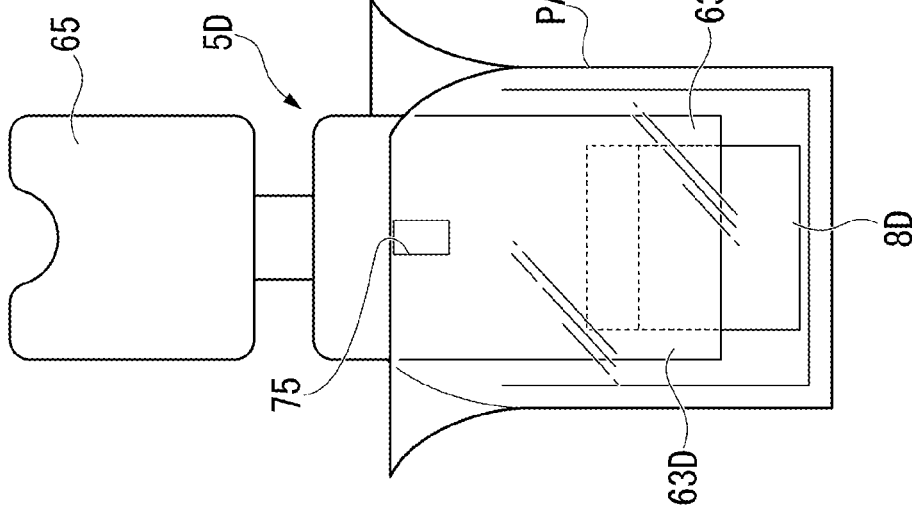
FIG. 47 is a diagram illustrating a method of storing the clip unit enclosed in the sterilized pack in the cartridge.
Figure 46:
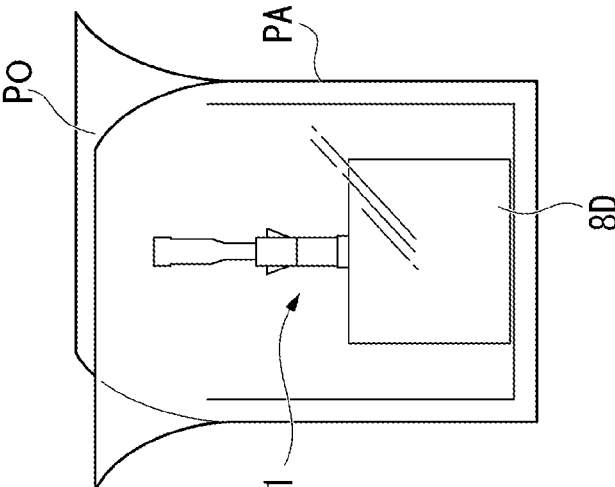
FIG. 46 is a diagram illustrating a method of storing the clip unit enclosed in the sterilized pack in the cartridge.

FIGS. 46 to 48 are diagrams illustrating a method of storing a clip unit 1 enclosed in a sterilized pack PA in the cartridge 5D. A user can unseal the unsealing opening PO of the sterilized pack PA, insert the cartridge 5D into the sterilized pack PA, and attach the auxiliary cartridge 8D to the arm accommodation portion 63D. The user can store the clip unit 1 in the storage area 7S without taking out the clip unit 1 from the sterilized pack PA.

Modified Example 4

Figure 49:
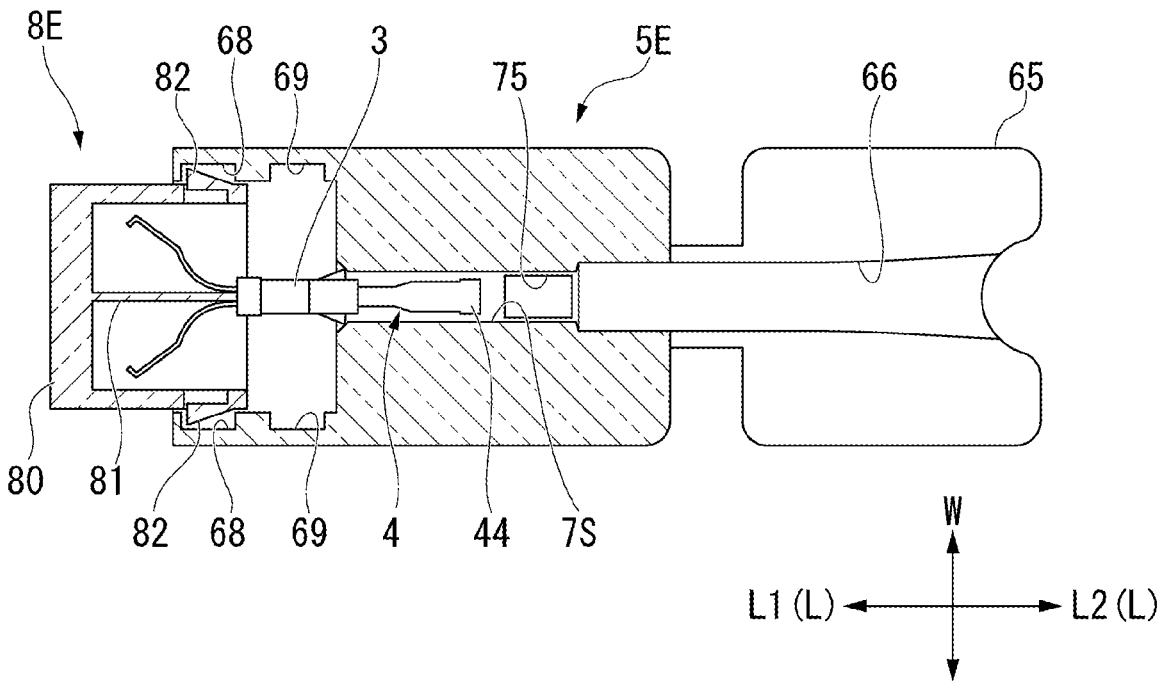
FIG. 49 is a diagram illustrating a modified example of the cartridge and a modified example of an auxiliary cartridge.
Figure 50:
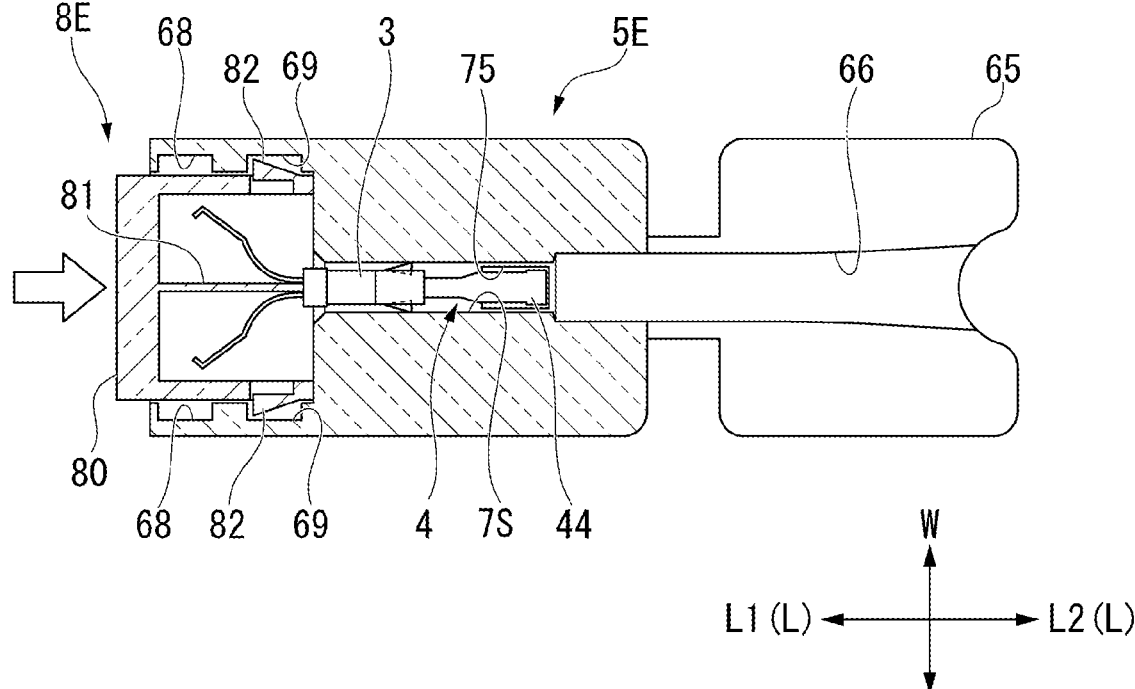
FIG. 50 is a diagram illustrating a modified example of the cartridge and a modified example of an auxiliary cartridge.

FIGS. 49 and 50 are diagrams illustrating a cartridge 5E which is a modified example of the cartridge 5D and an auxiliary cartridge 8E which is a modified example of the auxiliary cartridge 8D. The auxiliary cartridge 8E may further include a stopper 82 that can protrude and retract outward in the width direction W. The cartridge 5E may further includes a tip-side engagement portion 68 and a base-side engagement portion 69 that can engage with the stopper 82 in the arm accommodation portion 63D. The tip-side engagement portion 68 may be formed on the tip side L1 of the base-side engagement portion 69. The stopper 82 may be formed in a shape which can be easily pushed from the tip side L1 to the base side L2.

As illustrated in FIG. 49, when the stopper 82 engages with the tip-side engagement portion 68, the clip unit 1 may not completely stored in the storage area 7S. For example, the cartridge 5E and the auxiliary cartridge 8E may be closed in a sterilized pack PA in a state in which the stopper 82 can engage with the tip-side engagement portion 68.

As illustrated in FIG. 50, a user can push the auxiliary cartridge 8E from the tip side L1 to the base side L2 until the stopper 82 engages with the base-side engagement portion 69. When the stopper 82 engages with the base-side engagement portion 69, the clip unit 1 can be completely stored in the storage area 7S, and the connection arm 44 of the connection member 4 of the clip unit 1 can be disposed in the second area 72.

Modified Example 5

Figure 51:
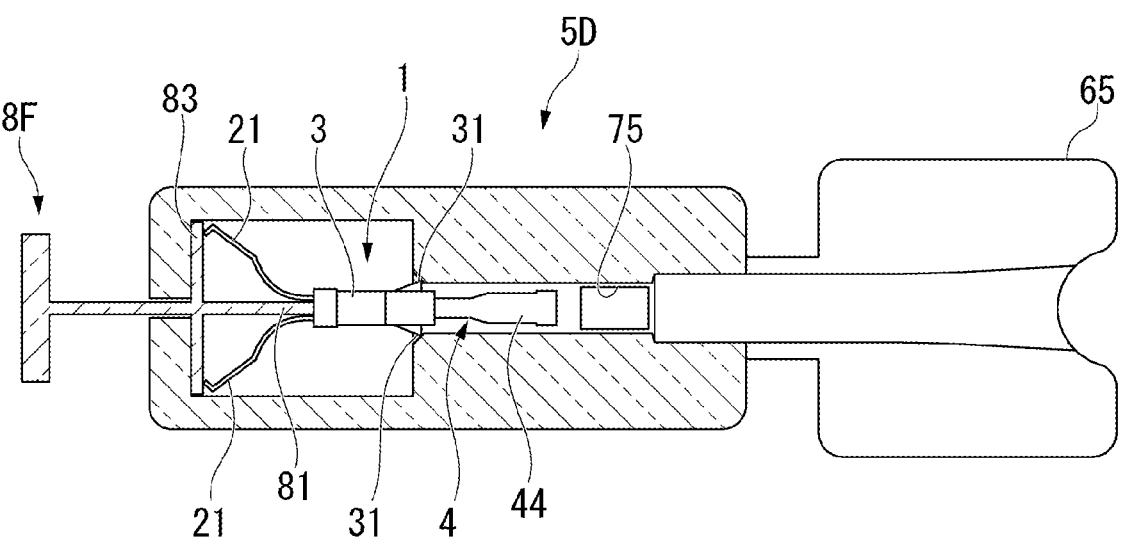
FIG. 51 is a diagram illustrating another modified example of the auxiliary cartridge.
Figure 52:
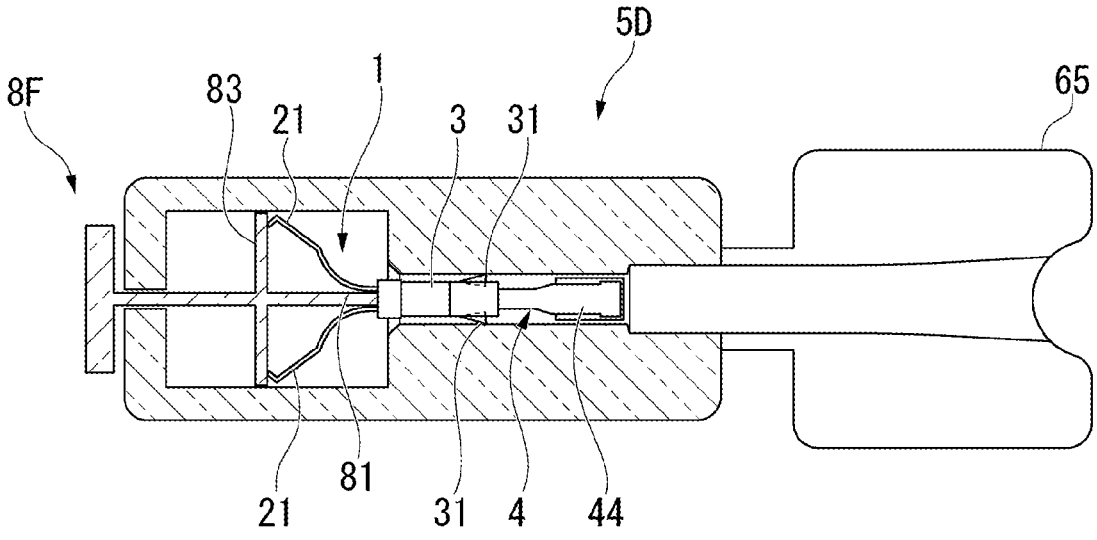
FIG. 52 is a diagram illustrating the modified example.

FIGS. 51 and 52 are diagrams illustrating an auxiliary cartridge 8F which is a modified example of the auxiliary cartridge 8D. The auxiliary cartridge 8F may include a front wall 83 engaging with the tips of a pair of arms 21. As illustrated in FIG. 51, a central protrusion 81 of the auxiliary cartridge 8F can come into contact with the tip opening 3a of the presser tube 3, and the front wall 83 can come into contact with the tips of the pair of arms 21. As illustrated in FIG. 52, a user can push the auxiliary cartridge 8F from the tip side L1 to the base side L2 until the clip unit 1 is completely stored in the storage area 7S. In such an example, the clip unit 1 does not move forward in the length direction (moving direction) L due to the central protrusion 81 and the front wall 83, and a user can easily load the clip unit 1 into the clip introduction device 200.

Modified Example 6

Figure 53:
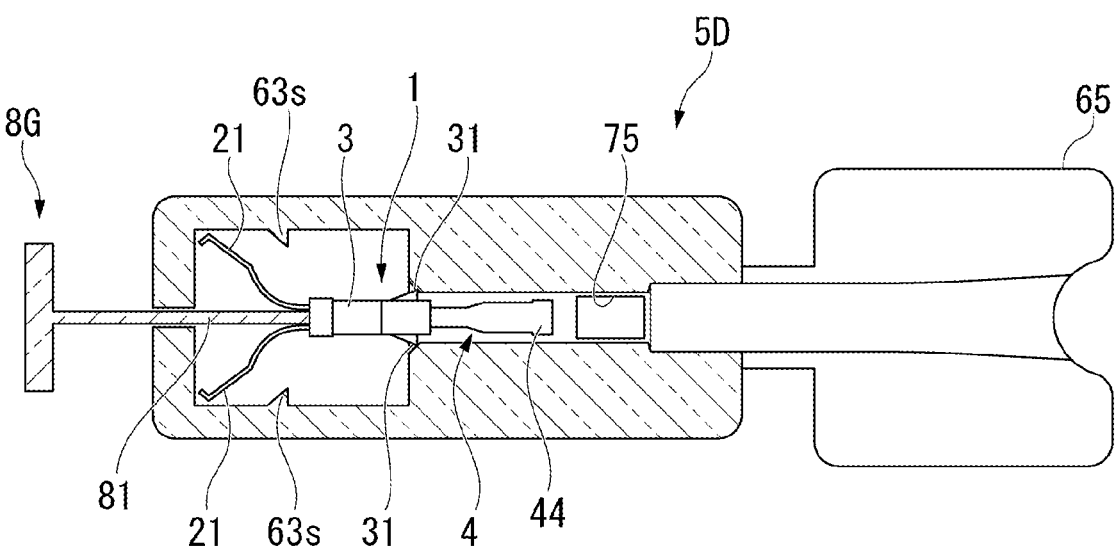
FIG. 53 is a diagram illustrating another modified example of the auxiliary cartridge.
Figure 54:
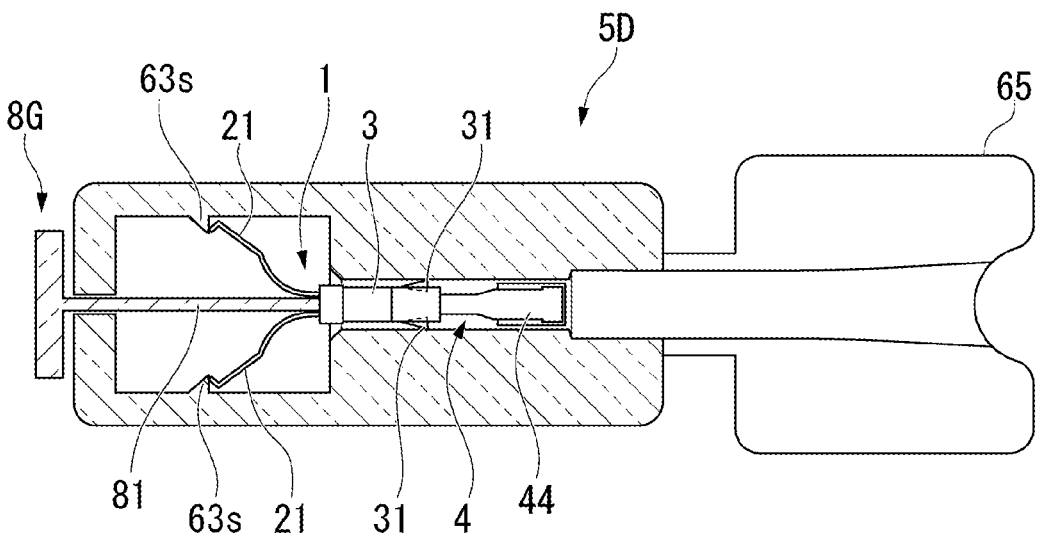
FIG. 54 is a diagram illustrating the modified example.
Figure 55:
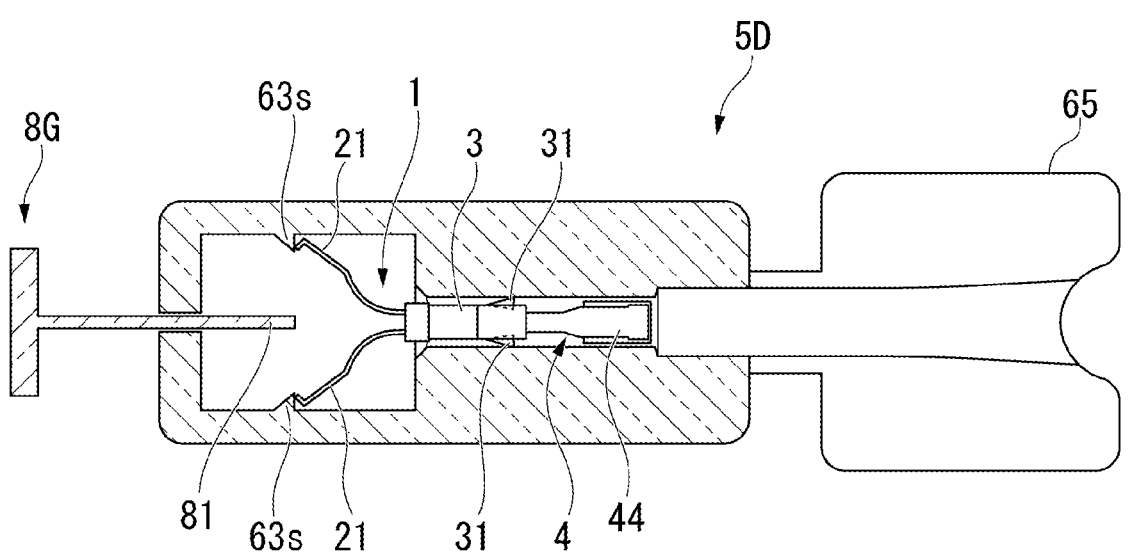
FIG. 55 is a diagram illustrating the modified example.

FIGS. 53 to 55 are diagrams illustrating an auxiliary cartridge 8G which is a modified example of the auxiliary cartridge 8D. The auxiliary cartridge 8G may not include the front wall 83 in comparison with the auxiliary cartridge 8F. However, the tips of a pair of arms 21 of the clip unit 1 pushed to the base side L2 by the auxiliary cartridge 8G can engage with stoppers 63s formed in the arm accommodation portion 63D. In this case, even when the auxiliary cartridge 8G is detached from the cartridge 5D, a state in which the clip unit 1 is positioned such that the connection arm 44 of the connection member 4 can disposed in the second area 72 is maintained.

Modified Example 7

Figure 56:
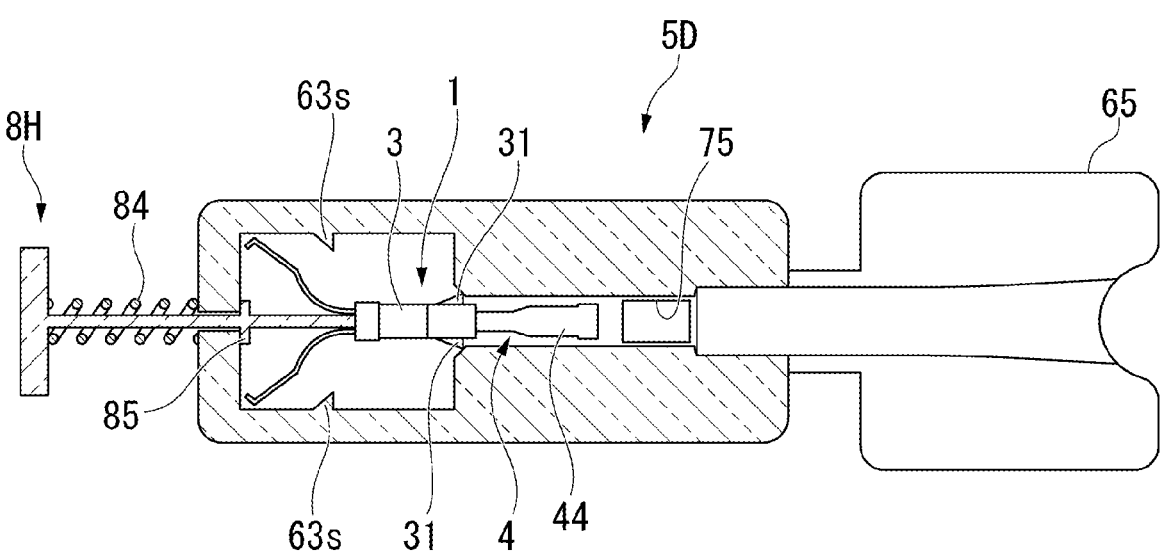
FIG. 56 is a diagram illustrating another modified example of the auxiliary cartridge.
Figure 57:
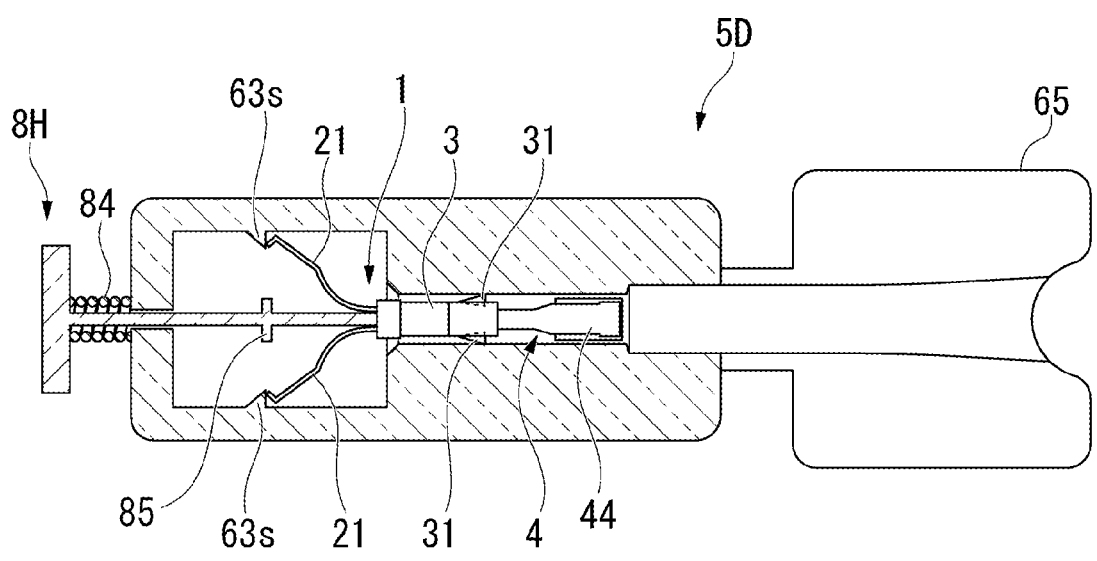
FIG. 57 is a diagram illustrating the modified example.
Figure 58:
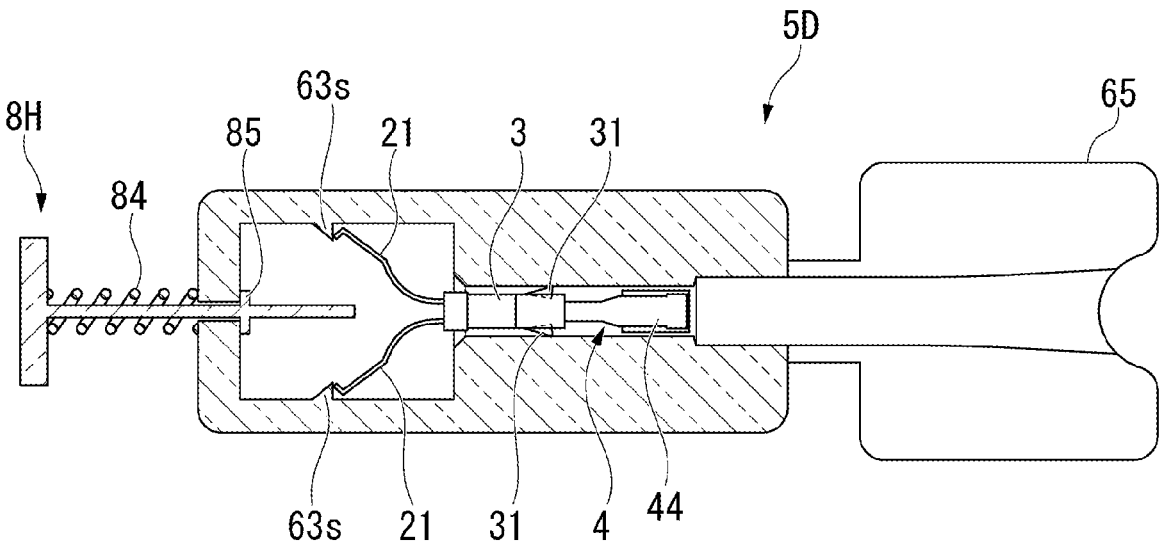
FIG. 58 is a diagram illustrating the modified example.

FIGS. 56 to 58 are diagrams illustrating an auxiliary cartridge 8H which is a modified example of the auxiliary cartridge 8D. The auxiliary cartridge 8H may include a spring 84 for biasing the auxiliary cartridge 8H to the tip side L1 in comparison with the auxiliary cartridge 8G. A user can push the auxiliary cartridge 8H from the tip side L1 to the base side L2. The tips of a pair of arms 21 of the clip unit 1 pushed to the base side L2 by the auxiliary cartridge 8H can engage with the stoppers 63s formed in the arm accommodation portion 63D. The auxiliary cartridge 8H can move to the tip side L1 with a restoring force of the spring 84. Accordingly, when the clip unit 1 is loaded into the clip introduction device 200, the pair of arms 21 may not interfere with the auxiliary cartridge 8H. The auxiliary cartridge 8H may include a stopper 85 and may not detach from the cartridge 5D even when the auxiliary cartridge 8H moves to the tip side L1 with the restoring force of the spring 84.

Modified Example 8

In the aforementioned embodiments, the clip unit is a re-graspable (e.g., re-openable) clip unit in which a pair of arms 21 has a self-expanding force, but the clip unit is not limited to this mode. The clip unit may be a clip unit which is not re-openable as described in Japanese Patent No. 4700608.

EXPLANATION OF REFERENCES

100, 100B, 100C, 100D . . . Cartridge system
200 . . . Clip introduction device (applicator)
300 . . . Clip device
1 . . . Clip unit
2 . . . Clip
3 . . . Presser tube
4 . . . Connection member
5, 5B, 5C, 5D, 5E . . . Cartridge
51 . . . First path, clip unit path
52 . . . Second path, sheath path
6, 6B . . . First cartridge
60 . . . Cartridge outer circumferential portion
60a . . . Tip
60b . . . Tip opening
60B . . . cartridge outer circumferential portion
60e . . . Base end
60u . . . Top surface
61 . . . Second cartridge support portion
62 . . . Second cartridge accommodation portion
63, 63B, 63D . . . Arm accommodation portion
63a . . . Wall
63s . . . Stopper
64 . . . Sheath insertion portion
65 . . . Compression portion
651 . . . First compression portion
652 . . . Second compression portion
65a . . . Connection portion
65b . . . Gap
66 . . . Sheath connection portion
66a . . . Straight portion
66b . . . Tapered portion
67 . . . Insertion port
68 . . . Tip-side engagement portion
69 . . . Base-side engagement portion
7, 7B . . . Second cartridge
7S . . . Storage area
70 . . . Cartridge body
70a . . . Tip
70b . . . Clip unit insertion port
70c . . . Tapered portion
71 . . . First area
72 . . . Second area
73 . . . Sheath insertion area
75, 75B . . . Recessed portion area
75u, 75Bu . . . Upper recessed portion area
75d, 7Bd . . . Lower recessed portion area

76 . . . Sheath contact portion
8D, 8E, 8F, 8G, 8H . . . Auxiliary cartridge
80 . . . Auxiliary cartridge body
81 . . . Central protrusion
82 . . . Stopper
83 . . . Anterior wall
84 . . . Spring
85 . . . Stopper The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:
1. A cartridge comprising:
a cartridge body having a storage area configured to store at least a part of a clip unit;
a first cartridge configured to store the cartridge body; and
an insertion port into which the clip unit is inserted into the storage area, wherein the storage area includes:
a first area configured to retract wings of the clip unit and configured to prevent a connection arm from connecting to an applicator; and
a second area configured to connect the connection arm with the applicator, wherein the cartridge body is rotatably supported by the first cartridge, wherein the cartridge body is movable between a first position and a second position relative to the first cartridge, and wherein the insertion port is farther from the first cartridge in the second position than in the first position.

2. The cartridge according to claim 1, wherein the second area forms a hollow area of which a section perpendicular to a moving direction of the clip unit has a substantially circular shape, wherein the second area includes a recessed portion in a height direction perpendicular to the moving direction, and wherein a length in the height direction of the second area in which the recessed portion is formed is larger than an inner diameter of the second area.

3. The cartridge according to claim 2, wherein the recessed portion is a through-hole formed on both sides in the height direction of the second area.

4. The cartridge according to claim 1, wherein the cartridge body is stored in the first cartridge when the cartridge body is located at the first position, and wherein the insertion port through which the clip unit is inserted into the storage area moves away from the first cartridge when the cartridge body is located at the second position.

5. The cartridge according to claim 4, wherein the first cartridge includes an arm accommodation portion configured to accommodate a tip of an arm of the clip unit, and wherein the arm accommodation portion and the storage area form a first path through which the clip unit is movable when a second cartridge is located at the first position.

6. The cartridge according to claim 4, further comprising:
a sheath connection portion configured to receive a sheath of the applicator, wherein the storage area includes a sheath insertion area contacting the second area, and wherein the sheath insertion area and the sheath connection portion form a second path into which the sheath is inserted when a second cartridge is located at the first position.

7. The cartridge according to claim 1, further comprising a sheath connection portion configured to receive a sheath of an applicator, wherein the first cartridge includes the sheath connection portion.

8. The cartridge according to claim 1, wherein, in a longitudinal direction of the first cartridge, a distance between the insertion port and the first cartridge in the second position is greater than a distance between the insertion port and the first cartridge in the first position.

9. The cartridge according to claim 1, wherein, in a direction intersecting a longitudinal direction of the first cartridge, a distance between the insertion port and the first cartridge in the second position is greater than a distance between the insertion port and the first cartridge in the first position.

10. A cartridge system comprising:
a clip unit including:
a clip;
a pipe including wings configured to protract and retract;
a connector including a connection arm configured to be connected to an applicator by closing and released from the applicator by opening, wherein closing couples the connection arm to the applicator, and wherein opening decouples the connection arm from the applicator, wherein a direction in which the connection arm is opened and closed is different from a direction in which the wings protrude and retract;
a cartridge body having a storage area configured to movably store at least a part of the clip unit; and
a sheath connection portion configured to receive a sheath of the applicator wherein, when the clip unit is stored in the storage area, the storage area includes:
a first area configured to retract the wings and configured to prevent the connection arm from connecting to the applicator;
a second area configured to keep the wings retracted and configured to connect the connection arm with the applicator;
a first cartridge including the sheath connection portion; and
a second cartridge including the cartridge body, wherein the storage area contacts the sheath connection portion by disposing the second cartridge at a first position at which the second cartridge is located in the first cartridge.

11. The cartridge system according to claim 10, wherein the direction in which the connection arm is opened and closed is perpendicular to the direction in which the wings protrude and retract.

12. The cartridge system according to claim 10, wherein the clip unit is enclosed in a pack along with the second cartridge in a state in which at least a part of the clip unit is stored in the storage area of the second cartridge detached from the first cartridge.

13. The cartridge system according to claim 10, wherein the second cartridge is rotatably supported by the first cartridge, and wherein the second cartridge is configured to move between the first position and a second position at which an insertion port through which the clip unit is inserted into the storage area moves away from the first cartridge.

14. A cartridge system comprising:
a pack;
a clip unit including a clip, a pipe including wings configured to protrude and retract, and a connector including a connection arm that is configured to be connected to an applicator; and
a second cartridge configured to be located in a first cartridge including a sheath connection portion into which a sheath of the applicator is inserted, wherein the clip unit is enclosed in a pack along with the second cartridge in a state in which at least a part of the clip unit is stored in the second cartridge detached from the first cartridge.

15. The cartridge system according to claim 14, wherein the second cartridge is rotatably supported by the first cartridge.

16. The cartridge system according to claim 15 wherein the second cartridge is configured to move between a first position and a second position at which an insertion port through which the clip unit is inserted into a storage area moves away from the first cartridge.

17. The cartridge system according to claim 16, wherein the storage area includes a first area and a second area.

18. The cartridge system according to claim 17, wherein the connection arm is configured to be connected to the applicator by closing and released from the applicator by opening, and in the first area the connection arm cannot transition to an open state.

19. The cartridge system according to claim 14, wherein the connection arm is configured to be connected to the applicator by closing and released from the applicator by opening, and a direction in which the connection arm is opened and closed is different from a direction in which the wings protrude and retract.

\* \* \* \* \*